(12) United States Patent
Oh et al.

(10) Patent No.: US 12,091,453 B2
(45) Date of Patent: Sep. 17, 2024

(54) EPITOPE SPECIFIC TO SMO PROTEIN, ANTIBODY RECOGNIZING SAME, AND COMPOSITION COMPRISING SAME

(71) Applicant: HEDGEHOG, INC., Seoul (KR)

(72) Inventors: Sang Cheul Oh, Seoul (KR); Dae-Hee Lee, Gyeonggi-do (KR)

(73) Assignee: HEDGEHOG, INC., Seoul (KR)

( * ) Notice: Subject to any disclaimer, the term of this patent is extended or adjusted under 35 U.S.C. 154(b) by 690 days.

(21) Appl. No.: 17/259,243

(22) PCT Filed: Jul. 11, 2019

(86) PCT No.: PCT/KR2019/008603
§ 371 (c)(1),
(2) Date: Jan. 11, 2021

(87) PCT Pub. No.: WO2020/013644
PCT Pub. Date: Jan. 16, 2020

(65) Prior Publication Data
US 2022/0213185 A1  Jul. 7, 2022

(30) Foreign Application Priority Data

Jul. 11, 2018 (KR) .................. 10-2018-0080489
Jul. 11, 2019 (KR) .................. 10-2019-0083901

(51) Int. Cl.
| C07K 16/28 | (2006.01) |
| A61K 31/7088 | (2006.01) |
| A61P 35/00 | (2006.01) |
| C07K 14/705 | (2006.01) |
| G01N 33/574 | (2006.01) |

(52) U.S. Cl.
CPC .......... *C07K 16/28* (2013.01); *A61K 31/7088* (2013.01); *A61P 35/00* (2018.01); *C07K 14/705* (2013.01); *G01N 33/574* (2013.01)

(58) Field of Classification Search
CPC .................................................. C07K 16/28
See application file for complete search history.

(56) References Cited

U.S. PATENT DOCUMENTS

| 8,481,680 | B2 | 7/2013 | de Sauvage |
| 9,676,850 | B2 * | 6/2017 | Saunders ............... C07K 16/28 |
| 2014/0178373 | A1 | 6/2014 | Kobayashi |

FOREIGN PATENT DOCUMENTS

WO     98/14475     4/1998

OTHER PUBLICATIONS

Wang et. al. (Nat. Commun. 5:1-20 (2014) (Year: 2014).*
Chiu et al., Antibodies, 8(55):1-80. (2019) (Year: 2019).*
Abnova Cat# H00006608-M09, RRID:AB_607067 (Year: 2014).*
Benchsci for H00006608-M09 (Year: 2024).*
Yeo et. al. (Biotechnol. J. 12(12):1-11 (2017)) (Year: 2017).*
Wu, F., et al., "Hedgehog Signaling: From Basic Biology to Cancer Therapy," Cell Chemical Biology, Mar. 2017, vol. 24, pp. 252-280.f.
Nehme, R., et al., "Stability study of the human G-protein coupled reception Smoothened," Biochimica et Biophysica Acta, 2010, vol. 1798, pp. 110-1110.
Anti-Smoothened antibody ab72130, ABCAM.
Bhave, V.S., et al., "Regulation of Liver Growth by Glypican 3, CD81, Hedgehog, and Hhex," The American Journal of Pathology, Jul. 2017, vol. 183, No. 1, pp. 153-159.
Shao, J., et al., "Aberrant Expression of PCTH (Patched Gene) and Smo (Smoothened Gene) in Human Pancreatic Cancerous Tissues and Its Association with Hyperglycemia," Pancreas, Jul. 2006, vol. 33, No. 1, pp. 38-44.
Srivatsan, S., et al., "Allogeneic tumor cell vaccines," Human Vaccines & Immunotherapeutics, Jan. 2014, vol. 10, Issue 1, pp. 52-63.
Shi, Y., et al., "The Side Population in Human Lung Cancer Cell Ling NCI-H460 Is Enriched in Stem-Like Cancer Cells," PLoS ONE, Mar. 2012, vol. 7, Issue 3, pp. 1-8.
Hirotsu, M., et al., "Smoothened as a new therapeutic target for human osteosarcoma," Molecular Cancer, 2020, vol. 9, No. 5, pp. 2-14.
Wang, F., et al., "Hedgehog Signaling Regulates Epithelial-Mesenchymal Transition in Pancreatic Cancer Stem-Like Cells," Journal of Cancer, 2020, vol. 7, pp. 408-417.
Martinez, M.C., et al., "Transfer of differentiation signal by membrane microvesicles harboring hedgehog morphogens," Blood, Nov. 2006, vol. 108, No. 9, pp. 3012-3020.
Byrne, E.F.X, et al., "Structural basis for smoothened regulation by its extracellular domains," Nature, Jul. 28, 2016, vol. 535, pp. 517-522 with Extended Data Figures 1-9.
Rohatgi, R., et al., "Hedgehog signal transduction by Smoothened: Pharmacologic evidence for a 2-step activation process," PNAS, Mar. 3, 2009, vol. 106, No. 9, pp. 3196-3201.
Nachtergaele, S., et al., "Structure and function of the Smoothened extracellular domain in vertebrate Hedgehog signaling," eLIFE, 2013, 2:e01340.

(Continued)

*Primary Examiner* — Jessica H Roark
*Assistant Examiner* — Francesca Edgingtongiordano
(74) *Attorney, Agent, or Firm* — DUANE MORRIS LLP; Gregory M. Lefkowitz; Brandon A. Chan

(57) ABSTRACT

The present invention identifies the influence of the TGFβ/Smad3/SMO molecular mechanism in cancer cells and elucidates that a high expression level of SMO is associated with the overall survival rate of cancer patients, demonstrating that SMO is a potential prognostic marker for cancer. The present invention relates to a specific epitope of SMO as an antigen and an antibody or a fragment thereof recognizing and binding specifically to the epitope. Therefore, the antibody of the present invention is expected to be useful as a therapeutic agent for SMO-related cancers.

18 Claims, 19 Drawing Sheets

Specification includes a Sequence Listing.

(56) References Cited

OTHER PUBLICATIONS

GenBank: AAD17202.1, smoothened [*Homo sapiens*], Jun. 10, 2016.
Giege, R., et al., "Crystallogenesis of Biological Macromolecules: Facts and Perspectives," Acta Crystallographica Section D. 1994, D50, 339-350.
McPherson, A., "Current approaches to macromolecular crystallization," Eur. J. Biochem., 1990, 189, 1-23.
Chayen, N.E., "The role of oil in macromolecular crystallization," Structure, Oct. 15, 1997, vol. 5, No. 10, pp. 1269-1274.
McPherson, A., "Crystallization of Proteins from Polyethylene Glycol," The Journal of Biological Chemistry, Oct. 25, 1976, vol. 251, No. 20, pp. 6300-6303.
Peng, S., et al., "A combination of DNA vaccines targeting human papillomavirus type 16 E6 and E7 generates potent antitumor effects," Gene Therapy, 2006, vol. 13, pp. 257-265.
He, X., et al., "Characterization of 7A7, an anti-mouse EGFR monoclonal antibody proposed to be the mouse equivalent of cetuximad," Oncotarget, 2018, vol. 9, No. 15, pp. 12250-12260.
Krupa, et al., "Immunization with recombinant DNA modified vaccinia virus Ankara(MVA) vectors delivering PSCA and STEAP1 antigens inhibits prostate cancer progression," Vaccine, 2011, vol. 29(7), pp. 1504-1513.
Yang, B., et al., "Effects of SMO polyclonal antibody on proliferation and invasive ability of prostate cancer DU145 cells," Journal of Tongji University (Medical Edition), Apr. 2017, 38(2); 39-44.

\* cited by examiner

1) Peptide 1 (α1)

2) Peptide 2 (α2)

3) Peptide 3 (α3)

EPITOPE SPECIFIC TO SMO PROTEIN, ANTIBODY RECOGNIZING SAME, AND COMPOSITION COMPRISING SAME

CROSS-REFERENCE TO RELATED APPLICATIONS

This application is a § 371 national stage entry of International Application No. PCT/KR2019/008603, filed on Jul. 11, 2019, which claims priority to South Korean Patent Application No. 10-2018-0080489, filed on Jul. 11, 2018, and South Korean Patent Application No. 10-2019-0083901, filed on Jul. 11, 2019, the entire contents of which are incorporated herein by reference.

SEQUENCE LISTING

The instant application contains a Sequence Listing which has been submitted electronically in ASCII format and is hereby incorporated by reference in its entirety. Said ASCII text file, created on Aug. 12, 2021, is named G1035-17901_SequenceListing. txt and is 19,193 bytes in size.

TECHNICAL FIELD

The present invention relates to a tumor-specific epitope of Smoothened (SMO) protein and a monoclonal antibody specifically binding to the epitope. More specifically, the present invention relates to an antibody that binds specifically to an epitope of SMO protein involved in the hedgehog signaling pathway to block the hedgehog signaling mechanism, thus being useful for targeted treatment of drug-resistant cancers as well as general cancers.

BACKGROUND ART

Cancer is the first leading cause of death in South Korea. Particularly, colorectal cancer is the most frequent cancer with the highest mortality rate in South Korea. Most recently, the incidence and mortality of colorectal cancer in South Korea have increased dramatically. In South Korea, many cases are diagnosed as having colorectal cancer through an early screening program by colonoscopy before surgery is impossible and are treated in the early stages of the disease.

Nevertheless, 1 out of 4 or 5 cancer patients suffer from metastases to other organs at the time of diagnosis and are diagnosed as Stage 4, which is difficult to treat by surgery. Therapeutic methods and agents for cancer have been developed in various aspects but most of them have been used alone or in appropriate combination with surgery, chemotherapy, and radiotherapy depending on the cancer stage. Therapeutic methods for cancer according to stages are roughly as follows: follow-up after curative surgery for stage 1 cancer (e.g., colorectal cancer); chemotherapy after curative surgery for stage 2 cancer (e.g., colorectal cancer); and chemotherapy according to patients' performance status for stage 4 cancer (e.g., colorectal cancer). It should be understood that even for stage 4 cancer, palliative surgery and radiotherapy can be further performed independently or in combination with each other if required.

Recently developed therapeutic methods for cancer are effective in extending the survival period of patients or alleviating the symptoms of the disease compared to previous ones considering that the primary goals of treatment of general cancer patients are to extend the survival period of the patients and alleviate the symptoms of the disease, but their anti-cancer effects are still unsatisfactory for complete treatment.

Many targeted therapeutic agents have been developed, such as bevacizumab (trade name: Avastin) and cetuximab (trade name: Erbitux). Specifically, bevacizumab was developed based on understanding of the interaction between cancer cells and vascular endothelial growth factor (VEGF). Bevacizumab is an anticancer drug that inhibits the growth and metastasis of cancer cells by blocking the VEGF pathway to suppress angiogenesis. Bevacizumab is mainly administered in combination with other anticancer drugs to enhance its therapeutic effects. VEGF-targeted therapeutic agents such as bevacizumab are currently used without diagnosis such as specific genetic testing because a predictive index has not been established to predict their effects.

In addition, cetuximab (trade name: Erbitux) is an anti-cancer drug that effectively blocks the signal transduction system of cancer cells to inhibit cancer growth and is a typical targeted therapeutic agent for colorectal cancer. Cetuximab is an antibody against the epidermal growth factor receptor and is effective in suppressing the growth of cancer cells by preventing the growth factor from signaling cells to divide.

Numerous studies are currently underway around the world to develop effective methods and drugs for the treatment of drug-resistant cancers and recurrent cancers as well as general cancers. However, most cancer therapeutic approaches are focused on the reduction of cancer size and studies on drug-resistant cancers and recurrent cancers still remain in the early stages. A particularly important consideration in determining the stage of cancer is not the size of cancer but the extent to which cancer penetrates the tissue.

Thus, there arises a need to identify biomolecules associated with the general symptoms of cancer, such as cancer growth, metastasis, and resistance and discover new biomarkers for targeted cancer therapy that target the biomolecules and can control both growth and metastasis of general and resistant cancers.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

An object of the present invention is to provide a novel use of a SMO epitope that inhibits the growth and metastasis of general cancer and resistant cancer through the hedgehog signaling mechanism.

Means for Solving the Problems

The inventors of the present invention have found that SMO protein is associated with the growth and metastasis of drug-resistant cancer as well as general cancer in the hedgehog (Hh) signaling pathway. The inventors of the present invention have also earnestly conducted research to discover new biomarkers for targeted cancer therapy that target SMO protein and can control both growth and metastasis of general and resistant cancer, and as a result, succeeded in finding a SMO epitope that inhibits the growth and metastasis of general and resistant cancers through the hedgehog signaling mechanism. The present invention has been accomplished based on these findings.

One aspect of the present invention provides an epitope including 1 to 10 amino acids selected from the amino acids at positions 106 to 485 of SMO protein having the sequence set forth in SEQ ID NO: 1.

A further aspect of the present invention provides an antibody or a fragment thereof that recognizes a SMO epitope having the sequence set forth in any one of SEQ ID NOS: 2 to 15 as an antigen and binds specifically to the SMO epitope wherein the antibody includes HCDR1 having the sequence set forth in SEQ ID NO: 16, HCDR2 having the sequence set forth in SEQ ID NO: 17, HCDR3 having the sequence set forth in SEQ ID NO: 18, LCDR1 having the sequence set forth in SEQ ID NO: 19, LCDR2 having the sequence set forth in SEQ ID NO: 20, and LCDR3 having the sequence set forth in SEQ ID NO: 21.

Another aspect of the present invention provides an antibody or a fragment thereof that recognizes a SMO epitope having the sequence set forth in any one of SEQ ID NOS: 2 to 15 as an antigen and binds specifically to the SMO epitope wherein the antibody cross-competes for binding to the SMO protein epitope with a reference antibody including HCDR1 having the sequence set forth in SEQ ID NO: 16, HCDR2 having the sequence set forth in SEQ ID NO: 17, HCDR3 having the sequence set forth in SEQ ID NO: 18, LCDR1 having the sequence set forth in SEQ ID NO: 19, LCDR2 having the sequence set forth in SEQ ID NO: 20, and LCDR3 having the sequence set forth in SEQ ID NO: 21.

Another aspect of the present invention provides a nucleic acid molecule encoding the antibody or fragment thereof.

Another aspect of the present invention provides a vector including the nucleic acid molecule.

Another aspect of the present invention provides a vaccine composition for preventing or treating cancer, including an epitope including 1 to 10 amino acids selected from the amino acids at positions 106 to 485 of SMO protein having the sequence set forth in SEQ ID NO: 1 and a carrier.

Another aspect of the present invention provides a composition including the antibody, the nucleic acid molecule or the vector.

Another aspect of the present invention provides a novel use of a composition for preventing or treating general or metastatic cancer, including the antibody, the nucleic acid molecule or the vector.

Yet another aspect of the present invention provides a method for preventing or treating general or metastatic cancer, including administering the composition.

Effects of the Invention

The features and advantages of the present invention are summarized as follows:

(i) The monoclonal antibody or fragment thereof according to the present invention recognizes and binds specifically to a SMO epitope as an antigen. The nucleic acid molecule of the present invention encodes the monoclonal antibody.

(ii) The antibody of the present invention binds specifically to an epitope of SMO protein, suppresses the hedgehog signaling pathway, and inhibits the activity of SMO protein. Based on its functions, the antibody of the present invention can be used to provide a vaccine or therapeutic agent for general cancer, resistance cancer, recurrent cancer or metastatic cancer in which SMO protein and the hedgehog signaling pathway is involved.

BEST MODE FOR CARRYING OUT THE INVENTION

Figure 1:
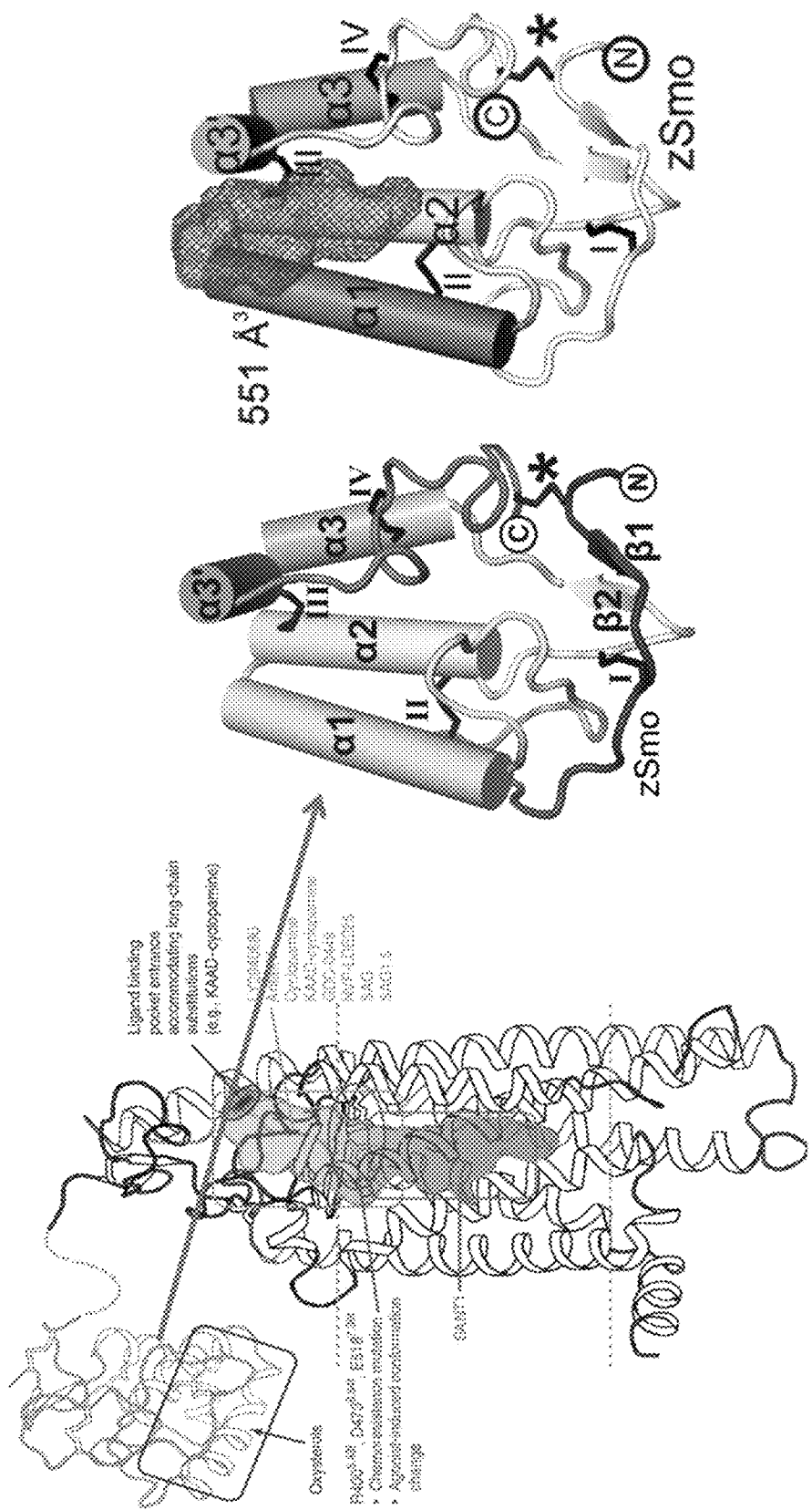
FIG. 1 shows the structure of SMO protein in which a SMO epitope is sequenced from an oxysterol-SMO binding site as the primary mechanism of SMO activity and the positions of α1, α2, and α3 peptides at a SMO receptor-oxysterol binding site are shown by computer simulation.
Figure 2:
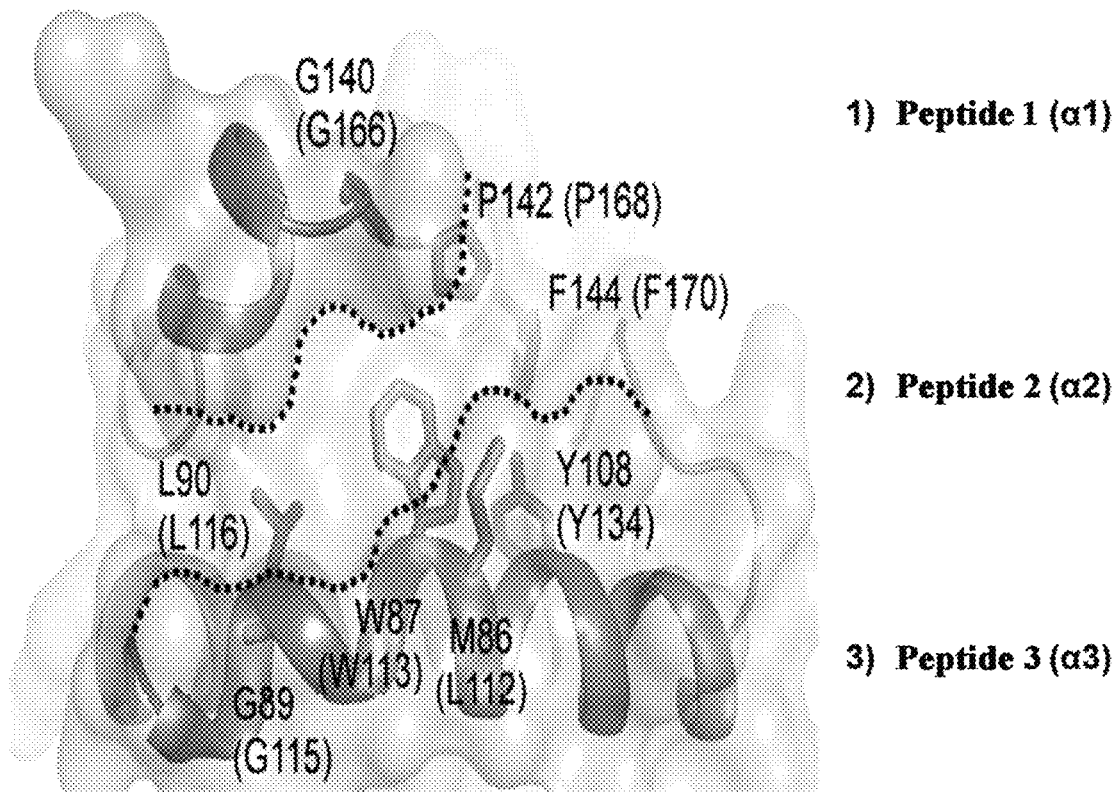
FIG. 2 is a diagram showing the structure of a mouse antibody produced from α1, α2, α3 peptides.

Other objects and advantages of the invention become more apparent from the following detailed description, claims, and drawings.

One aspect of the present invention provides an epitope including 1 to 10 amino acids selected from the amino acids at positions 106 to 485 of SMO protein having the sequence set forth in SEQ ID NO: 1.

Hedgehog (Hh) is a protein that plays an essential role in embryonic development. Hedgehog acts on the development of various organs, including the dorsal and ventral axes and organs in the nervous and musculoskeletal systems. Hedgehog in adult tissues is involved in the maintenance of stem cells and its abnormal hyperactivity is known to cause various cancers such as basal cell cancer and cerebral cancer. After the development process, hedgehog signaling activity is maintained only in some specific adult tissues and decreases in most somatic cells. Mutations of hedgehog signaling genes (Ptch, Smo, Sufu, Gli, etc.) at the somatic stage cause aberrant signaling activity, resulting in carcinogenesis.

The hedgehog signaling pathway is initiated by the binding of Sonic hedgehog to Patched1 (Ptch1), a 12-transmembrane receptor present in the cell membrane. Ptch1 has an inhibitory effect on SMO, a 7-transmembrane Gli protein-coupled receptor. However, when Sonic hedgehog binds to Ptch1, Ptch1 loses its inhibitory activity on SMO, resulting in the activation of SMO. Once activated, SMO activates Gli, a transcription factor, to activate the expression of the hedgehog target gene. In other words, hedgehog acting as a ligand binds to the Ptch1 receptor present in the cell membrane to promote the migration of SMO, a GPCR-like transmembrane protein whose activity is inhibited by Phch1, to primary cilia and the activity of the Gli transcription factor as a final hedgehog signaling effector.

SMO regulates the activity of Gli transcription factors as follows. SMO migrates to primary cilia by hedgehog and regulates Sufu, which inhibits the migration of Gli transcription factors to the nucleus in the downstream signaling stage, or increases the stability of Gli proteins in the primary cilia and converts inactive Gli to a transcriptionally active state. The activation of the Gli transcription factors induces an increase in the expression of genes affected by hedgehog to allow cell migration, proliferation, and differentiation processes to proceed.

As a result of extensive efforts to discover new antigens that can control cancer, the inventors of the present invention have succeeded in identifying a specific epitope of SMO protein associated with various cancers in the hedgehog signaling pathway (Sonic(SHH))/PATCHED/(PTCH1)/SMOOTHENED(SMO)) as an antigen to which an antibody targeting and capable of immunologically recognizing the SMO protein specifically binds, completing the present invention.

As used herein, the term "epitope" refers to a localized region of an antigen to which an antibody or a fragment thereof can specifically bind. Epitopes typically consist of molecular surface groups such as amino acids or sugar side chains and generally have specific three-dimensional structural characteristics and specific charge characteristics. Conformational and non-conformational epitopes are distinguished in that the binding to the former but not the latter is lost in the presence of denaturing solvents. The epitope may include amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The epitope of the present invention may include 1 to 10 amino acids selected from the amino acids at positions 106 to 115, 125 to 133, 159 to 166, 216 to 224, 299 to 307, 391 to 399, and 477 to 485 of SMO protein.

The epitope including the amino acids at the defined positions of SMO protein may be combined with a carrier in order to maintain its structure when used in a vaccine or a composition. The carrier is not particularly limited as long as it is biocompatible and can achieve the desired effects of the present invention. The carrier is preferably selected from peptide, serum albumin, immunoglobulin, hemocyanin, and polysaccharides.

Specifically, the epitope of the present invention consists of some or all of the amino acid residues present in the cysteine-rich domain (CRD) or pocket position (SMO-7TM) of Smoothened (SMO) protein, as shown in FIG. 1. The amino acid residues at positions 106 to 115 are LVLWSGLRNA (SEQ ID NO: 2), the amino acid residues at positions 125 to 133 are LLCAVYMPK (SEQ ID NO: 3), the amino acid residues at positions 159 to 166 are RERGWPDF (SEQ ID NO: 4), the amino acid residues at positions 216 to 224 are QCQNPLFTE (SEQ ID NO: 5), the amino acid residues at positions 299 to 307 are GTMRLGEPT (SEQ ID NO: 6), the amino acid residues at positions 391 to 399 are FVGYKNYRY (SEQ ID NO: 7), and the amino acid residues at positions 477 to 485 are QAEWERSFR (SEQ ID NO: 8). Preferably, the epitope of the present invention includes one, some or all of the amino acid sequences described above. The amino acid sequences may be contiguous or non-contiguous. Some of the amino acids in the sequences may be interchangeable.

The SMO protein may have the sequence set forth in SEQ ID NO: 1, which can be found in the GenBank database.

Smoothened (SMO) is a 7-transmembrane Gli protein-coupled receptor and is known to regulate the activity of Gli transcription factors, which are final effectors in the hedgehog signaling pathway. However, newly developed compounds for suppressing cancer caused by hedgehog signaling hyperactivity are only designed to target the activity of Ptch1 or hedgehog protein in the hedgehog signaling pathway or to suppress the inhibitory activity for SMO. These compounds fail to completely inhibit the hedgehog signaling pathway and are difficult to apply to drug-resistant cancer cells caused by SMO mutations. Thus, there is an urgent need to develop a SMO inhibitor that exhibits therapeutic effects against various types of cancers (including general, resistant, and recurrent cancers), as mentioned above.

A further aspect of the present invention provides an antibody or a fragment thereof that recognizes a SMO epitope having the sequence set forth in any one of SEQ ID NOS: 2 to 15 as an antigen and binds specifically to the SMO epitope wherein the antibody includes HCDR1 having the sequence set forth in SEQ ID NO: 16, HCDR2 having the sequence set forth in SEQ ID NO: 17, HCDR3 having the sequence set forth in SEQ ID NO: 18, LCDR1 having the sequence set forth in SEQ ID NO: 19, LCDR2 having the sequence set forth in SEQ ID NO: 20, and LCDR3 having the sequence set forth in SEQ ID NO: 21.

Another aspect of the present invention provides an antibody or a fragment thereof that recognizes a SMO epitope having the sequence set forth in any one of SEQ ID NOS: 2 to 15 as an antigen and binds specifically to the SMO epitope wherein the antibody cross-competes for binding to the SMO protein epitope with a reference antibody including HCDR1 having the sequence set forth in SEQ ID NO: 16, HCDR2 having the sequence set forth in SEQ ID NO: 17, HCDR3 having the sequence set forth in SEQ ID NO: 18, LCDR1 having the sequence set forth in SEQ ID NO: 19, LCDR2 having the sequence set forth in SEQ ID NO: 20, and LCDR3 having the sequence set forth in SEQ ID NO: 21.

Abnormal hyperactivity of hedgehog in adult tissues is known to cause various cancers such as basal cell cancer and cerebral cancer. There are three mammalian hedgehogs: Sonic, Indian, and Desert, of which the most studied one is the Sonic hedgehog (SHH) signaling pathway where the systemic expression of hedgehog can be found.

The Sonic hedgehog signaling pathway is initiated by the binding of Sonic hedgehog to Patched1 (Ptch1), a 12-transmembrane receptor present in the cell membrane. Ptch1 has an inhibitory effect on SMO, a 7-transmembrane Gli protein-coupled receptor. However, when Sonic hedgehog binds to Ptch1, Ptch1 loses its inhibitory activity on SMO, resulting in the activation of SMO. Once activated, SMO activates Gli, a transcription factor, to activate the expression of the hedgehog target gene. In other words, hedgehog acting as a ligand binds to the Ptch1 receptor present in the cell membrane to promote the migration of SMO, a GPCR-like transmembrane protein whose activity is inhibited by Phch1, to primary cilia and the activity of the Gli transcription factor as a final hedgehog signaling effector. SMO protein is most highly active in cancer cells and high expression or activation of SMO protein is associated with the low survival rate of cancer patients or cancer cells, as demonstrated in the Experimental Examples section that follows.

High expression of SMO protein was found to be associated with the low survival rate of colorectal cancer patients. It was also found that the expression of SMO protein increases in colorectal cancer cell lines compared to that in normal cells. It was also found that the expressions of SMO and GLI1 proteins as hedgehog signaling components increase in WIDR, SW48, SNUC2A, colo205, SNU283, SW480, SW620, HCT8, SNUC1, and LS174T colorectal cancer cell lines. These results reveal that Gil protein, a final hedgehog signaling effector, is regulated by the activation of SMO protein. It was also found that an antibody specifically binds to an epitope region of SMO protein to inhibit or suppress the activation of the SMO protein. The present invention has been accomplished based on these findings.

According to preferred embodiments of the present invention, the antigen-binding protein binds specifically to and suppresses or inhibits SMO protein having the sequence set forth in SEQ ID NO: 1 and is not particularly limited as long as it is produced using SMO protein or a portion thereof (epitope) as an antigen.

As used herein, the term "epitope" refers to a localized region of an antigen to which an antibody or a fragment thereof can specifically bind. For example, the epitope may consist of contiguous amino acids of the polypeptide antigen. Alternatively, the epitope may consist of two or more non-contiguous regions by tertiary folding in the polypeptide. The epitope may include at least 2, at least 3, at least 4, at least 5, at least 6, at least 7, at least 8, at least 9 or at least 10 contiguous or non-contiguous amino acids in a unique spatial conformation of the antigen. The antibody or fragment thereof according to the present invention recognizes and binds specifically to SMO as an antigen and can specifically bind to the epitope consisting of 1 to 10 amino acids selected from the amino acid residues at positions 106 to 485 of the SMO protein. The epitope may include one or more amino acids.

Methods for determining what epitopes are bound by a given antibody (i.e., epitope mapping) are well known in the art and include, for example, immunoblotting and immunoprecipitation assays. Methods of determining spatial conformation of epitopes include various techniques, for example, x-ray crystallography, 2-dimensional nuclear magnetic resonance and HDX-MS (Epitope Mapping Protocols in Methods in Molecular Biology, Vol. 66, G. E. Morris, Ed. (1996)).

According to preferred embodiments of the present invention, the epitope to which the antibody or fragment thereof according to the present invention can bind can be determined by, e.g., NMR spectroscopy, X-ray diffraction crystallography studies, ELISA assays, hydrogen/deuterium exchange coupled with mass spectrometry (HDX-MS), array-based oligo-peptide scanning assays, and/or mutagenesis mapping (Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303).

As used herein, the term "antibody" can be of any type (e.g., IgG, IgE, IgM, IgD, IgA or IgY) or any subclass (e.g., IgG1, IgG2, IgG3 and IgG4 in humans, and IgG1, IgG2a, IgG2b and IgG3 in mice) of immunoglobulin molecule. Immunoglobulins (e.g., IgG1) exist in several allotypes. The term "antibody" may be of the IgG1, IgG2, IgG3 or IgG4 subclass or any hybrid thereof (e.g., a hybrid of IgG2 and IgG4).

The term "monoclonal antibody" as used herein refers to an antibody that displays a single binding specificity and affinity for a particular epitope.

The monoclonal antibody of the present invention can be produced by a hybridoma technique, which was first introduced in Kohler et al., Nature 256, 495 (1975), or a recombinant DNA technique. The monoclonal antibody can be isolated from phage antibody libraries by techniques described, for example, in Clackson et al., Nature 352, 624-628 (1991) and Marks et al., J. Mol. Biol. 222, 581-597 (1991). The monoclonal antibody can be produced from a suitable source. The monoclonal antibody of the present invention can be produced from a hybridoma obtained from cells expressing a SMO antigen or cells obtained from a mouse immunized with an antigen of interest in the form of nucleic acids encoding a SMO antigen. The monoclonal antibody can also be produced from a hybridoma derived from antibody-expressing cells from an immunized human or non-human mammal (such as a rat, a dog or a primate).

The monoclonal antibody is herein meant to include its fragments. Preferably, the fragments mean antigen binding fragments. The fragment can be prepared by various methods known in the art. For example, Fab and F(ab')2 fragments can be produced by proteolytic cleavage of immunoglobulin molecules, using enzymes such as papain (to produce Fab fragments) or pepsin (to produce F(ab')2 fragments).

The term "fragment" may be a Fab, a Fab', a F(ab')2, a Fv, a single chain Fv (scFv), or a sdAb consisting of a monomeric VH or VL domain. Such fragments are well known in the art.

The monoclonal antibody or fragment thereof according to the present invention includes an antigen binding protein that binds to an epitope of SMO protein having the sequence set forth in SEQ ID NO: 1 and inhibits physiological effects associated with SMO-mediated cancer growth and metastasis. Specifically, the expression of Gli protein as a final effector increases through the activation of the hedgehog signaling mechanism in cancer. SMO expression by hedgehog is involved in this process. The activation or expression of SMO protein increases Gli protein in the hedgehog signaling pathway and causes cancer. That is, SMO protein is increased or activated by the hedgehog signaling mechanism to affect cancer growth and development. The treatment with the monoclonal antibody, including the antigen-binding protein, or fragment thereof is useful for suppressing and inhibiting the expression or activity of SMO protein.

As used herein, the term "inhibits growth" is intended to include any measurable decrease in the growth of cells upon contact with the monoclonal antibody or fragment thereof according to the present invention as compared to the growth of the same cells not in contact with the monoclonal antibody or fragment thereof (e.g., inhibition of cell growth in a cell culture medium by about 10%, 20%, 30%, 40%, 50%, 60%, 70%, 80%, 90% or 100%). The decrease in cell growth can be achieved by a variety of mechanisms.

The antigen binding protein includes one or more CDRs (e.g., 1, 2, 3, 4, 5, or 6 CDRs). The antigen binding protein is a polypeptide that binds to SMO as an antigen and includes one or more complementarity determining regions (CDRs) as described herein. The CDRs are oriented in the antigen binding protein to achieve suitable antigen binding characteristics. The antigen binding protein disclosed herein can inhibit, block, reduce or regulate the expression or activation of SMO. As a result, the antigen binding protein can inhibit SMO present in a subject to suppress cancer development, growth, and metastasis mediated by the hedgehog signaling pathway.

A disorder in the regulation of the hedgehog signaling pathway is known to contribute to the occurrence of resistant cancer to chemotherapy and radiotherapy, recurrent cancer or metastatic cancer. Although the fundamental resistance mechanism has not been clearly established, administration of the SMO antibody according to the present invention to cancer cells resistant to conventional anticancer drugs was found to significantly suppress the growth of the cancer cells. In conclusion, the antibody or fragment thereof according to the present invention has significant therapeutic effects for resistant, recurrent and metastatic cancers as well as general cancers.

A VH domain, or one or more CDRs thereof, can be linked to a constant domain for forming a heavy chain. A VL domain, or one or more CDRs thereof, can be linked to a constant domain for forming a light chain. A full length heavy chain and full length light chain combine to form a full length antibody.

As described above, the antigen-binding protein binds to the epitope including 1 to 10 amino acids selected from the amino acid residues at positions 106 to 485 of SMO protein having the sequence set forth in SEQ ID NO: 1. The antigen-binding protein specifically binding to SMO is effective in suppressing, blocking, and inhibiting the hedgehog signaling pathway and the expression and activation of SMO protein.

Preferably, the antigen-binding protein has sequences complementary to all or some of the amino acid sequences set forth in SEQ ID NOS: 2 to 15, enabling its specific or selective binding to SMO protein.

The antigen-binding protein can be used for therapeutic use due to its ability to suppress, inhibit or regulate one or more biological activities of SMO. The antigen-binding protein binds specifically to SMO protein and substantially suppresses SMO, which was demonstrated through in vitro competitive binding in the Experimental Examples section that follows.

Variable regions of immunoglobulin chains generally exhibit the same overall structure, including relatively conserved framework regions (FR) joined by three hypervariable regions (more often called "complementarity determining regions" or CDRs). The CDRs from the two chains of each heavy chain/light chain pair mentioned above typically are aligned by the framework regions to form a structure that binds specifically with a specific epitope or domain on the target protein (e.g., PCSK9). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342: 878-883.

The various heavy chain and light chain variable regions can be provided herein. Each of these variable regions may be attached to the above heavy and light chain constant regions to form a complete antibody heavy and light chain, respectively. Further, each of the so generated heavy and light chain sequences may be combined to form a complete antibody structure.

According to preferred embodiments of the present invention, the antibody or fragment thereof is a SMO antibody including CDRs or variable regions disclosed herein that bind to the SMO epitope. In specific embodiments, the antibody or fragment thereof includes HCDR1, HCDR2 and HCDR3, and LCDR1, LCDR2 and LCDR3 wherein HCDR1, HCDR2, and HCDR3 include the amino acid sequences set forth in SEQ ID NOS: 16, 17, and 18, respectively, and LCDR1, LCDR2, and LCDR3 include the amino acid sequences set forth in SEQ ID NOS: 19, 20, and 21, respectively.

According to preferred embodiments of the present invention, the antibody or fragment thereof cross-competes for binding to the SMO epitope with (or inhibits binding of) a SMO antibody including the CDRs and variable regions disclosed herein. In certain embodiments, the antibody or fragment thereof inhibits binding of a reference antibody including HCDR1, HCDR2, and HCDR3 and LCDR1, LCDR2, and LCDR3 wherein HCDR1, HCDR2, and HCDR3 include the amino acid sequences set forth in SEQ ID NOs: 16, 17, and 18, respectively, and LCDR1, LCDR2, and LCDR3 include the amino acid sequences set forth in SEQ ID NOS: 19, 20, and 21, respectively.

In some embodiments, the reference antibody includes (1) a heavy chain variable region (VH) including the sequence set forth in SEQ ID NO: 22 and a light chain variable region (VL) including the sequence set forth in SEQ ID NO: 27; (2) a heavy chain variable region (VH) including the sequence set forth in SEQ ID NO: 23 and a light chain variable region (VL) including the sequence set forth in SEQ ID NO: 28; (3) a heavy chain variable region (VH) including the sequence set forth in SEQ ID NO: 24 and a light chain variable region (VL) including the sequence set forth in SEQ ID NO: 29; (4) a heavy chain variable region (VH) including the sequence set forth in SEQ ID NO: 25 and a light chain variable region (VL) including the sequence set forth in SEQ ID NO: 29; or (5) a heavy chain variable region (VH) including the sequence set forth in SEQ ID NO: 26 and a light chain variable region (VL) including the sequence set forth in SEQ ID NO: 29.

Preferably, the reference antibody includes (2) a heavy chain variable region (VH) including the sequence set forth in SEQ ID NO: 23 and a light chain variable region (VL) including the sequence set forth in SEQ ID NO: 28; (3) a heavy chain variable region (VH) including the sequence set forth in SEQ ID NO: 24 and a light chain variable region (VL) including the sequence set forth in SEQ ID NO: 29; (4) a heavy chain variable region (VH) including the sequence set forth in SEQ ID NO: 25 and a light chain variable region (VL) including the sequence set forth in SEQ ID NO: 29; or (5) a heavy chain variable region including the sequence set forth in SEQ ID NO: 26 (VH) and a light chain variable region including the sequence set forth in SEQ ID NO: 29 (VL). Most preferably, the reference antibody includes (4) a heavy chain variable region including the sequence set forth in SEQ ID NO: 25 (VH) and a light chain variable region (VL) including the sequence set forth in SEQ ID NO: 29 or (5) a heavy chain variable region (VH) including the sequence set forth in SEQ ID NO: 26 and a light chain variable region (VL) including the sequence set forth in SEQ ID NO: 29.

In certain embodiments, the antibody or fragment thereof according to the present invention inhibits binding of a reference antibody to SMO protein by at least 10%, 20%, 30%, 40%, 50%, 60%, 70%, 80%, 90% or 100%. Competing antibodies bind to the same epitope, an overlapping epitope or to adjacent epitopes (e.g., as evidenced by steric hindrance). Whether two antibodies compete with each other for binding to a target can be determined using competition experiments known in the art such as RIA and EIA.

The antibody or fragment thereof according to the present invention is capable of binding to at least one epitope of human SMO protein, for example, as determined by binding of the antibody to the fragment of the human SMO protein. In some embodiments, the antibody or fragment thereof binds to at least one epitope including 1 to 10 amino acids selected from the amino acid residues at positions 106 to 485 of SMO protein having the sequence set forth in SEQ ID NO: 1. In some embodiments, the antibody and fragment thereof bind to all or some of the amino acid sequences set forth in SEQ ID NOS: 2 to 15. According to preferred embodiments, the antibody of the present invention may bind to at least one SMO epitope having the sequences set forth in SEQ ID NOS: 9 to 13. In some embodiments, the at least one epitope has the amino acid sequence that is at least 90%, at least about 95%, at least about 96%, at least about 97%, at least about 98%, at least about 99%, or about 100% identical to SEQ ID NOS: 9 to 13.

A VH domain or one or more CDRs thereof described herein can also be linked to a constant domain for forming a heavy chain, e.g., a full length heavy chain. Similarly, a VL domain or one or more CDRs thereof described herein can be linked to a constant domain for forming a light chain, e.g., a full length light chain. A full length heavy chain and full length light chain combine to form a full length antibody.

According to preferred embodiments, the antibody of the present invention is a chimeric antibody, a human antibody or a humanized antibody.

Another aspect of the present invention provides a nucleic acid molecule encoding the polypeptide, a vector including the nucleic acid molecule or a host cell including the vector.

The nucleic acid molecule of the present invention may be an isolated or recombinant nucleic acid molecule. Examples of such nucleic acid molecules include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated. The isolated nucleic acid may be understood as a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame.

However, an enhancer needs not be contiguous. The linkage is performed by ligation at a convenient restriction enzyme site. In the case where this site does not exist, a synthetic oligonucleotide adaptor or a linker is used according to a suitable method known in the art.

As used herein, the term "vector" is used to refer to a carrier into which a nucleic acid sequence can be inserted for introduction into a cell where it can be replicated. A nucleic acid sequence can be "exogenous," or "heterologous". Vectors include plasmids, cosmids and viruses (e.g., bacteriophage). One of skill in the art may construct a vector through standard recombinant techniques (Maniatis et al., Molecular Cloning, A Laboratory Manual, Cold Spring Harbor Press, Cold Spring Harbor, N.Y., 1988; and Ausubel et al., In: Current Protocols in Molecular Biology, John, Wiley & Sons, Inc, N Y, 1994, etc.).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "regulatory sequences". In addition to regulatory sequences that govern transcription and translation, vectors and expression vectors may contain nucleic acid sequences that serve other functions as well.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

The host cell of the present invention is preferably a bacterial cell, CHO cell, HeLa cell, HEK293 cell, BHK-21 cell, COS7 cell, COPS cell, A549 cell or NIH3T3 cell, but is not limited thereto.

Another aspect of the present invention provides a vaccine composition for preventing or treating cancer, including an epitope including 1 to 10 amino acids selected from the amino acids at positions 106 to 485 of SMO protein having the sequence set forth in SEQ ID NO: 1, a nucleic acid molecule encoding the epitope or a vector including the nucleic acid molecule.

The nucleic acid molecule of the present invention may be an isolated or recombinant nucleic acid molecule. Examples of such nucleic acid molecules include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated. The isolated nucleic acid may be understood as a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame.

However, an enhancer needs not be contiguous. The linkage is performed by ligation at a convenient restriction enzyme site. In the case where this site does not exist, a synthetic oligonucleotide adaptor or a linker is used according to a suitable method known in the art.

As used herein, the term "vector" is used to refer to a carrier into which a nucleic acid sequence can be inserted for introduction into a cell where it can be replicated. A nucleic acid sequence can be "exogenous," or "heterologous". Vectors include plasmids, cosmids and viruses (e.g., bacteriophage). One of skill in the art may construct a vector through standard recombinant techniques (Maniatis et al., Molecular Cloning, A Laboratory Manual, Cold Spring Harbor Press, Cold Spring Harbor, N.Y., 1988; and Ausubel et al., In: Current Protocols in Molecular Biology, John, Wiley & Sons, Inc, N Y, 1994, etc.).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "regulatory sequences". In addition to regulatory sequences that govern transcription and translation, vectors and expression vectors may contain nucleic acid sequences that serve other functions as well.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

The host cell of the present invention is preferably a bacterial cell, CHO cell, HeLa cell, HEK293 cell, BHK-21 cell, COS7 cell, COPS cell, A549 cell or NIH3T3 cell, but is not limited thereto.

The vaccine may be a live vaccine, an attenuated vaccine or a dead vaccine.

The vaccine composition of the present invention can induce not only an immune response but also a systemic immune response to SMO protein through active immunity to prevent or treat cancer. Active immunity means that an individual produces his own antibodies when exposed to a pathogen.

The vaccine composition of the present invention can be administered to a subject to prevent or treat cancer.

The cancer can be selected from the group consisting of brain tumor, melanoma, myeloma, non-small cell lung cancer, oral cancer, liver cancer, gastric cancer, colon cancer, breast cancer, lung cancer, bone cancer, pancreatic cancer, skin cancer, head cancer, neck cancer, cervical cancer, ovarian cancer, colorectal cancer, small intestine cancer, rectal cancer, fallopian tube carcinoma, anal cancer, endometrial carcinoma, vaginal carcinoma, vulvar carcinoma, Hodgkin's disease, esophageal cancer, lymph node cancer, bladder cancer, gallbladder cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, kidney cancer, ureteral cancer, renal cell carcinoma, renal pelvic carcinoma, central nervous system tumor, primary central nervous system lymphoma, spinal cord tumor, brainstem glioma, pituitary adenoma, lymphoma, leukemia, and multiple myeloma. The cancer may be an advanced cancer, resistant cancer, recurrent cancer or metastatic cancer. In particular, the resistant cancer refers to a drug-resistant cancer. Suitable therapeutic drugs for resistant cancers include, but are not particularly limited to, nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine, vorinostat, entinostat, 5FU and carmustine. Preferably, the recurrent cancer is a cancer resistant to oxaliplatin or cetuximab.

Another aspect of the present invention provides a composition including the antibody or fragment thereof, the nucleic acid molecule, the vector or an inhibitor inhibiting the expression of SMO gene.

According to preferred embodiments, the composition of the present invention is a pharmaceutical composition for preventing or treating cancer, suppressing the metastasis of cancer or preventing or treating resistant, recurrent or metastatic cancer.

Another aspect of the present invention provides a novel use of the or fragment thereof, the nucleic acid molecule, the vector or an inhibitor inhibiting the expression of SMO gene for the manufacture of a medicament for preventing or treating cancer, suppressing the metastasis of cancer or preventing or treating resistant, recurrent or metastatic cancer.

The cancer can be selected from the group consisting of brain tumor, melanoma, myeloma, non-small cell lung cancer, oral cancer, liver cancer, gastric cancer, colon cancer, breast cancer, lung cancer, bone cancer, pancreatic cancer, skin cancer, head cancer, neck cancer, cervical cancer, ovarian cancer, colorectal cancer, small intestine cancer, rectal cancer, fallopian tube carcinoma, anal cancer, endometrial carcinoma, vaginal carcinoma, vulvar carcinoma, Hodgkin's disease, esophageal cancer, lymph node cancer, bladder cancer, gallbladder cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, kidney cancer, ureteral cancer, renal cell carcinoma, renal pelvic carcinoma, central nervous system tumor, primary central nervous system lymphoma, spinal cord tumor, brainstem glioma, pituitary adenoma, lymphoma, leukemia, and multiple myeloma. The cancer may be an advanced cancer, resistant cancer, recurrent cancer or metastatic cancer. In particular, the resistant cancer refers to a drug-resistant cancer. Suitable therapeutic drugs for resistant cancers include, but are not particularly limited to, nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, capecitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine, vorinostat, entinostat, 5FU and carmustine. Preferably, the recurrent cancer is a cancer resistant to oxaliplatin or cetuximab.

The pharmaceutical composition of the present invention may include (a) the antibody or fragment thereof, the nucleic acid molecule, the vector including the nucleic acid molecule or an inhibitor inhibiting the expression of SMO gene and (b) a pharmaceutically acceptable carrier.

The cancer is caused by overexpression of SMO gene or protein. The SMO gene can be found in the GenBank database.

The term "overexpression" is used to represent a cancer in which SMO protein is overexpressed and means that the expression level of SMO is at least 1.1 times, preferably at least 2 times higher than that in comparative cells (e.g., normal colorectal cells), as measured by a suitable expression assay.

The greatest feature of the composition according to the present invention is that the composition targets SMO gene or protein and inhibits the expression level of the SMO gene or the expression or activity of the SMO protein to treat cancer, inhibit cancer metastasis or treat resistant, recurrent or metastatic cancer.

The inhibitor may be selected from the group consisting of small interference RNA (siRNA), short hairpin RNA (shRNA), microRNA (miRNA), ribozyme, DNAzyme, peptide nucleic acid (PNA), antisense oligonucleotide, and combinations thereof. The inhibitor is preferably a short hairpin RNA or small hairpin RNA (shRNA) that binds specifically to the mRNA of the gene. The inhibitor can inhibit the expression of the SMO gene.

Another aspect of the present invention provides a method for preventing or treating cancer, including administering the pharmaceutical composition. Another aspect of the present invention provides a method for preventing or treating metastatic cancer, including administering the pharmaceutical composition.

The type of cancer to be prevented or treated by the present invention is not limited. The pharmaceutical composition of the present invention can be administered to treat a variety of cancers, including common adult solid tumors selected from the group consisting of brain tumor, melanoma, myeloma, non-small cell lung cancer, oral cancer, liver cancer, gastric cancer, colon cancer, breast cancer, lung cancer, bone cancer, pancreatic cancer, skin cancer, head cancer, neck cancer, cervical cancer, ovarian cancer, colorectal cancer, small intestine cancer, rectal cancer, fallopian tube carcinoma, anal cancer, endometrial carcinoma, vaginal carcinoma, vulvar carcinoma, Hodgkin's disease, esophageal cancer, lymph node cancer, bladder cancer, gallbladder cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, kidney cancer, ureteral cancer, renal cell carcinoma, renal pelvic carcinoma, central nervous system tumor, primary central nervous system lymphoma, spinal cord tumor, brainstem glioma, pituitary adenoma, lymphoma, leukemia, and multiple myeloma.

The pharmaceutical composition has therapeutic effects against advanced, resistant, recurrent or metastatic cancer. In particular, the resistant cancer refers to a drug-resistant cancer. Suitable therapeutic drugs for resistant cancers include, but are not particularly limited to, nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, capecitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine, vorinostat, entinostat, 5FU and carmustine. Preferably, the recurrent cancer is a cancer resistant to oxaliplatin or cetuximab.

Each of the vaccine composition and the pharmaceutical composition according to the present invention may include one or more pharmaceutically acceptable carriers that are commonly used for formulation. Examples of the pharmaceutically acceptable carriers include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in Remington's Pharmaceutical Sciences (19th ed., 1995).

The vaccine composition and the pharmaceutical composition of the present invention can be administered orally or parenterally, preferably parenterally. Examples of suitable parenteral routes of administration include intravenous injection, local injection, and intraperitoneal routes.

Suitable dosages of the vaccine composition and the pharmaceutical composition according to the present invention may vary depending on factors such as formulation, mode of administration, patient's age, weight, sex, pathological condition, and diet, time of administration, route of administration, excretion rate, and responsiveness. A skilled physician can easily determine and prescribe doses of the vaccine composition and the pharmaceutical composition according to the present invention effective for desired treatment and prevention. According to preferred embodiments, each of the vaccine composition and the pharmaceutical composition according to the present invention may be administered in a daily dosage of 0.0001 to 100 mg/kg.

Each of the vaccine composition and the pharmaceutical composition of the present invention can be formulated with one or more pharmaceutically acceptable carriers and/or excipients in accordance with methods that can be easily carried out by those skilled in the art. The vaccine composition and the pharmaceutical composition can be provided in unit dosage forms or dispensed in multi-dose containers. The formulation may be in the form of a solution, suspension or emulsion in an oil or aqueous medium or may be in the form of an extract, powder, granule, tablet or capsule. The formation may further include a dispersant or a stabilizer.

Each of the vaccine composition and the pharmaceutical composition of the present invention may be used alone or in combination with one or more other conventional chemotherapies and/or radiotherapies. This combination therapy is more effective for cancer treatment. Chemotherapeutic agents can be used in combination with the compositions of the present invention. Examples of the chemotherapeutic agents include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, and methotrexate. Radiotherapies can be used in combination with the compositions of the present invention. For example, the radiotherapies may be X-ray irradiation and γ-ray irradiation.

Another aspect of the present invention provides a method for quantifying SMO protein in a sample, including treating a sample isolated from a subject with the antibody or fragment thereof.

The antibody or fragment thereof according to the present invention can be used to accurately measure the expression level of SMO protein in the sample due to its ability to specifically bind to the SMO protein. In addition, the use of the antibody or fragment thereof ensures the measurement of the expression levels of SMO protein associated with drug-resistant, recurrent or metastatic cancer.

Another aspect of the present invention provides a method for providing information for the diagnosis of a disease caused by overexpression of SMO protein, including (a) isolating a sample from a subject, (b) treating the sample with the antibody or fragment thereof or the nucleic acid molecule encoding the antibody or fragment thereof, and (c) determining whether the expression level of SMO in the sample is higher than that of SMO in a sample from a normal group.

SMO protein is involved in the hedgehog signaling pathway and converts Gli as a final effector to a transcriptionally active state to promote cell migration, proliferation and differentiation processes. SMO protein is overexpressed in a variety of cancers such as bladder cancer, lung cancer, ovarian cancer, renal cancer, colorectal cancer, prostate cancer, breast cancer, uterine cancer, rhabdomyosarcoma, and glioblastoma, drug-resistant cancers, metastatic cancers, and recurrent cancers. Since overexpressed SMO protein is directly involved in major cancer progression processes, such as proliferation, migration, penetration, and metastasis of cancer cells, a comparison of the expression level of SMO protein in the hedgehog signaling pathway with that in a healthy subject can provide information for the diagnosis of a disease caused by overexpression of SMO protein.

According to a preferred embodiment of the present invention, the disease caused by overexpression of SMO protein is a cancer.

The cancer can be selected from the group consisting of brain tumor, melanoma, myeloma, non-small cell lung cancer, oral cancer, liver cancer, gastric cancer, colon cancer, breast cancer, lung cancer, bone cancer, pancreatic cancer, skin cancer, head cancer, neck cancer, cervical cancer, ovarian cancer, colorectal cancer, small intestine cancer, rectal cancer, fallopian tube carcinoma, anal cancer, endometrial carcinoma, vaginal carcinoma, vulvar carcinoma, Hodgkin's disease, esophageal cancer, lymph node cancer, bladder cancer, gallbladder cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, kidney cancer, ureteral cancer, renal cell carcinoma, renal pelvic carcinoma, central nervous system tumor, primary central nervous system lymphoma, spinal cord tumor, brainstem glioma, pituitary adenoma, lymphoma, leukemia, and multiple myeloma. The cancer may be an advanced cancer, resistant cancer, recurrent cancer or metastatic cancer. In particular, the resistant cancer refers to a drug-resistant cancer. Suitable therapeutic drugs for resistant cancers include, but are not particularly limited to, nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, capecitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine, vorinostat, entinostat, 5FU and carmustine. Preferably, the recurrent cancer is a cancer resistant to oxaliplatin or cetuximab.

Yet another aspect of the present invention provides a kit for quantifying SMO protein, including the antibody or fragment thereof or the nucleic acid molecule encoding the antibody or fragment thereof.

The quantification kit of the present invention can quantify the amount of SMO protein by analyzing an antigen to the antibody through an antigen-antibody binding reaction. The antigen-antibody binding reaction is preferably selected from the group consisting of, but not limited to, enzyme-linked immunosorbent assay (ELISA), radioimmunoassay (MA), sandwich assay, Western blotting on polyacrylamide gel, immunoblotting assay, and immunohistochemical staining.

A support for the antigen-antibody binding reaction is selected from the group consisting of, but not limited to, nitrocellulose membranes, PVDF membranes, well plates made of polyvinyl or polystyrene resin, and slide glasses.

The secondary antibody is preferably labeled with a reagent that develops a color. The color-developing reagent can be selected from the group consisting of fluoresceins and dyes. The fluoresceins may be, for example, horseradish peroxidase (HRP), alkaline phosphatase, colloid gold, poly-L-lysine-fluorescein isothiocyanate (FITC), and rhodamine-B-isothiocyanate (RITC). A substrate for inducing color development is preferably used depending on the color-developing reagent. The substrate is preferably selected from the group consisting of, but not limited to, 3,3',5,5'-tetramethylbenzidine (TMB), 2,2'-azino-bis(3-ethylbenzothiazoline)-6-sulfonic acid (ABTS), and ophenylenediamine (OPD).

MODE FOR CARRYING OUT THE INVENTION

The present invention will be more specifically explained with reference to the following examples. It will be evident to those skilled in the art that the scope of the present invention is not limited by these examples according to the gist of the present invention.

Production Examples 1-5: Production of SMO Antibodies

Antibodies were produced by immunizing mice with ~15-mer amino acid residues of SMO protein having the sequence set forth in SEQ ID NO: 1 as an antigen. The antibody production was requested to BIOONE (Korea).
1) Immunization of Mice and Production of Hybridoma Cells SMO monoclonal antibodies were produced using amino acid residues at positions 100-115 (SEQ ID NO: 9; SMO antibody Nos. 21 and 283), amino acid residues at positions 214-228 (SEQ ID NO: 10, SMO antibody Nos. 324, 401, and 408), amino acid residues at positions 124-138 (SEQ ID NO: 11), amino acid residues at positions 155-169 (SEQ ID NO: 12), amino acid residues at positions 475-488 (SEQ ID NO: 13), amino acid residues at positions 389-403 (SEQ ID NO: 14), and amino acid residues at positions 297-310 (SEQ ID NO: 15) of SMO protein as an antigen. SEQ ID NOS: 9-15 were selected as target peptides for efficient antibody production.

After each of the target peptides (SEQ ID NOS: 9-15) for antibody production was injected into mice, antibody-producing cells (B cells, B lymphocytes) to the antigen were generated from the spleen of the mice. The antibody-producing cells were fused with myeloma cells to form hybridoma cells. After culture in HAT medium where only hybridoma cells can survive, the activity of the antibody was confirmed by an ELISA experiment.

2) Isolation and Characterization

Monoclonal hybridoma cells capable of specifically recognizing SMO protein were selected from the hybridoma cells and injected into the abdominal cavity of mice. Monoclonal antibodies were recovered from the ascites and purified using protein A and protein G columns. Thereafter, the monoclonal antibodies (SMO mAb) capable of specifically recognizing SMO were isolated and characterized by Western blotting and immunofluorescence using SMO construct and siRNA.

SMO antibody Nos. 21 (Production Example 1) and 283 (Production Example 2) were isolated and characterized from the amino acid residues at positions 100-115 (SEQ ID NO: 9) of SMO protein as an antigen. SMO antibody Nos. 324 (Production Example 3), 401 (Production Example 4), and 408 (Production Example 5) were isolated and characterized from the amino acid residues at positions 214-229 (SEQ ID NO: 10) of SMO protein as an antigen.

Production Examples 6-10: Production of Humanized SMO Antibody Nos. 5, 7, 15, 16, and 17

Antibodies were produced by immunizing mice with ~15-mer amino acid residues of SMO protein having the sequence set forth in SEQ ID NO: 1 as an antigen. The antibody production was requested to BIOONE (Korea).

1) Immunization of Mice and Production of Hybridoma Cells

Monoclonal antibodies were produced using amino acid residues at positions 100-115 (SEQ ID NO: 9) of SMO protein as an antigen. The amino acid residues were selected as target peptides for antibody production.

After each of the target peptides for antibody production was injected into mice, antibody-producing cells (B cells, B lymphocytes) to the antigen were generated from the spleen of the mice. The antibody-producing cells were fused with myeloma cells to form hybridoma cells. After culture in HAT medium where only hybridoma cells can survive, the activity of the antibody was confirmed by an ELISA experiment.

2) Isolation and Hybridoma Sequencing

Total RNA of anti-SMO antibody was extracted from $5 \times 10^6$ hybridoma cells and complementary DNA (cDNA) was synthesized from the total RNA using a cDNA synthesis kit (Roche) according to the manufacturer's instructions. Heavy chain variable region (VH) and light chain variable region (VL) coding regions were amplified by PCR using mouse Ig primers (Millipore). The PCR products were cloned into T vectors (Promega) for sequencing. The antibodies were sequenced and the results are presented in Table 1. CDR sequences were determined as described in Kabat et al., Sequences of Proteins of Immunological Interest, 5th Ed. Public Health Service, National Institutes of Health, Bethesda, MD (1991).

TABLE 1

| SEQ ID NO | Sequence |
|---|---|
| SEQ ID NO: 16 | EYTMH |
| SEQ ID NO: 17 | GINPNTGDTRYNQKFKG |
| SEQ ID NO: 18 | DYYGSPFVY |
| SEQ ID NO: 19 | RSSQSIVHSSGYTFLD |
| SEQ ID NO: 20 | KVSNRFS |
| SEQ ID NO: 21 | FQGSHVPLT |

3) Conversion to Humanized Antibodies

For humanized antibody production, the amino acid sequences of the heavy and light chain variable regions of the mouse SMO antibodies were compared with the amino acid sequences of human antibodies in the IMGT database. As a result of comparison and analysis, the heavy chain genes IGHV1-3*01, IGHV1-46*01, and IGHV1-69-2*01 and the light chain genes IGKV2-30*20, IGKV2D-28*01, and IGKV1-39*01 of the human antibody variable region with the highest similarity were selected. For humanization of the mouse SMO antibodies, the CDRs of the mouse SMO antibodies were inserted into the genes of the human antibody variable region and the amino acid residues of the humanized FR were replaced with those of the mouse antibodies. The full sequences of the humanized antibodies are shown in Table 2.

TABLE 2

| Antibody name | Sequences VH | VL |
|---|---|---|
| SMO No. 5 (huSM01-21-05) | SEQ ID NO: 22<br>EVQLVQSGAEVKKPGATVKIS<br>CKVSGYTFTEYTMHWVQQAP<br>GKGLEWMGGINPNTGDTRYN<br>QKFKGRVTITVDKSTDTAYME<br>LSSLRSEDTAVYYCARDYYGS<br>PFVYWGQGTLVTVSS | SEQ ID NO: 27<br>DVVMTQSPLSLPVTLGQPASISC<br>RSSQSIVHSSGYTFLDWFQQRPG<br>QSPRRLIYKVSNRFSGVPDRFSG<br>SGSGTDFTLKISRVEAEDVGVYY<br>CFQGSHVPLTFGGGTKVEIK |
| SMO No. 7 (huSM01-21-07) | SEQ ID NO: 23<br>QVQLVQSGAEVKKPGASVKVS<br>CKASGYTFTEYTMHWVRQAP<br>GQRLEWMGGINPNTGDTRYN<br>QKFKGRVTITVDKSASTAYME<br>LSSLRSEDTAVYYCARDYYGS<br>PFVYWGQGTLVTVSS | SEQ ID NO: 28<br>DIVMTQSPLSLPVTPGEPASISCR<br>SSQSIVHSSGYTFLDWYLQKPGQ<br>SPQLLIYKVSNRFSGVPDRFSGS<br>GSGTDFTLKISRVEAEDVGVYY<br>CFQGSHVPLTFGGGTKVEIK |

TABLE 2-continued

| Antibody name | Sequences | |
|---|---|---|
| | VH | VL |
| SMO No. 15 (huSM01-21-15) | SEQ ID NO: 24<br>QVQLVQSGAEVKKPGASVKVS<br>CKASGYTFTEYTMHWVRQAP<br>GQRLEWMGG<u>INPNTGDTRYN<br>QKFKG</u>RVTITVDKSASTAYME<br>LSSLRSEDTAVYYCAR<u>DYYGS<br>PFVYW</u>GQGTLVTVSS | SEQ ID NO: 29<br>DIQMTQSPSSLSASVGDRVTITC<br>RSS<u>QSIVHSSGYTFLDWY</u>QQKPG<br>KAPKLLIY<u>KVSNRFS</u>GVPSRFSG<br>SGSGTDFTLTISSLQPEDFATYYC<br><u>FQGSHVPLTF</u>GQGTKVEIK |
| SMO No. 16 (huSM01-21-16) | SEQ ID NO: 25<br>QVQLVQSGAEVKKPGASVKVS<br>CKASGYTF<u>TEYTMH</u>WVRQAP<br>GQGLEWMGG<u>INPNTGDTRYN<br>QKFKG</u>RVTMTVDKSTSTVYM<br>ELSSLRSEDTAVYYCAR<u>DYYG<br>SPFVYW</u>GQGTLVTVSS | |
| SMO No. 17 (huSM01-21-17) | SEQ ID NO: 26<br>EVQLVQSGAEVKKPGATVKIS<br>CKVSGYTF<u>TEYTMH</u>WVQQAP<br>GKGLEWMGG<u>INPNTGDTRYN<br>QKFKG</u>RVTITVDKSTDTAYME<br>LSSLRSEDTAVYYCAR<u>DYYGS<br>PFVYW</u>GQGTLVTVSS | |

The CDR1, 2, and 3 sequences are indicated by underlines.

EXAMPLES

<Example 1> Determination of Whether or not SMO Protein was Expressed in Colorectal Cancer Tissues 1. Targets 206 cases of colorectal cancer tissues were excised from colorectal cancer patients after surgery from 2005 to 2009 and 27 cases of colorectal tissues (normal tissues) obtained from locations more than 0.5 cm away from the tumors were used as controls.

2. Tissue Microarray Construction

The normal tissues and the colorectal cancer tissues were fixed in formaldehyde and embedded in paraffin. Each tissue was consecutively cut into four 3 μm-thick sections, which were attached to slides treated with 3-amino-propyltriethoxysilane. One of the sections was stained with 10% Mayer's hematoxylin and the other three sections were immunohistochemically stained for the SMO antigen. The cases on the hematoxylin-stained slides were histologically examined, representative regions were marked, and corresponding regions in the paraffin blocks were selected. The selected regions were punched to a 2 mm size using a microtome for tissue microarray block construction (MICROM international). Microholes with a diameter of 2 mm and a depth of 2 mm were drilled in previously prepared recipient blocks, and tissue pieces punched out from the case blocks were pulled into a total of 233 microholes. The tissue microarray block was left standing at 50° C. for 30 min to make the cross section planar.

3. Immunohistochemical Staining (IHC)

The tissue microarray slide was immersed in a citrate buffer solution (10 mM, pH 6.0) for antigen recovery and treated three times in a phosphate buffered solution (PBS, 10 mM, pH 6.0) using a microwave oven for 5 min each. Thereafter, the treated slide was added with 3% hydrogen peroxide, washed with PBS for 10 min, treated with 10% sheep serum to inhibit nonspecific binding, and treated with primary antibodies. Anti-SMO antibody (abcam, MA, USA) (1:50) was incubated at room temperature for 1 h. The antibody was washed three times with PBS, incubated with a secondary antibody (DAKO, Carpinteria, USA) at room temperature for 1 h, washed three times with PBS, and incubated with streptavidin-HRP (DAKO, Carpinteria, USA) for 10 min.

Thereafter, color was developed with 3,3'-diaminobenzydine (DAB), counter-stained with 10% Mayer's hematoxylin, washed with running water, mounted, and observed with an optical microscope.

4. Conclusion

Figure 3:
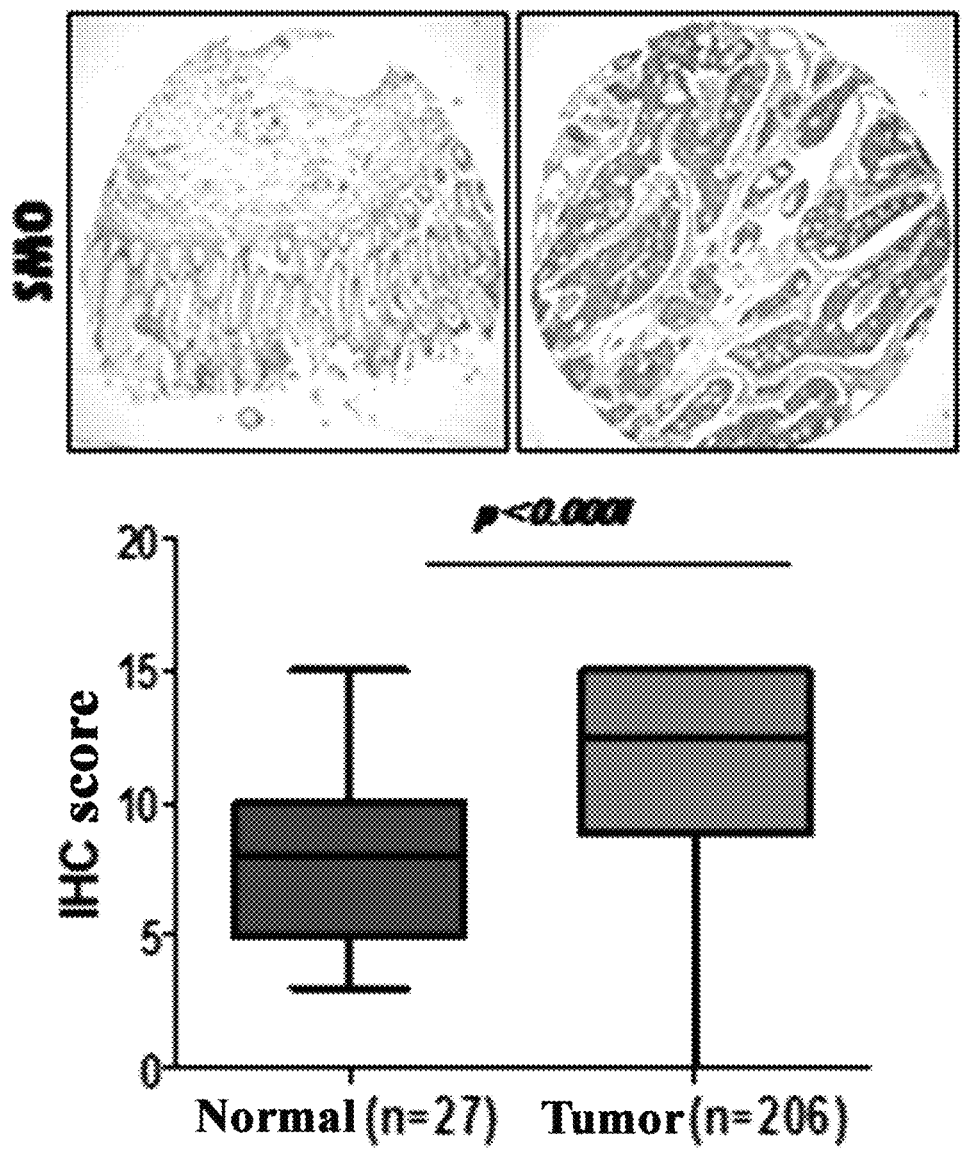
FIG. 3 shows optical microscopy images of randomly selected immunohistochemically stained sections of normal and colorectal cancer tissues (top) and a graph showing the results of immunohistochemical staining for the tissues (bottom).

FIG. 3 shows optical microscopy images of randomly selected immunohistochemically stained sections of the normal and colorectal cancer tissues (top) and a graph showing the results of immunohistochemical staining for the tissues (bottom). As shown in FIG. 3, the expression level of SMO protein in the colorectal cancer tissue was higher than that in the normal tissue. In particular, the staining intensity for SMO expression was statistically significantly higher in the colorectal cancer tissue ($p<0.0001$).

<Example 2> Determination of Survival Rates Depending on Expression Level of SMO in Colorectal Cancer Tissues The survival rates of 206 cases of colorectal cancer tissues obtained in Example 1 were analyzed depending on the expression level of SMO. The colorectal cancer tissues were divided into a group having low expression levels of SMO (SMO week, blue line) and a group having high expression levels of SMO (SMO strong, green line). The survival curves of the two groups were compared. The overall survival curves were analyzed using the statistical program SPSS.

Figure 4:
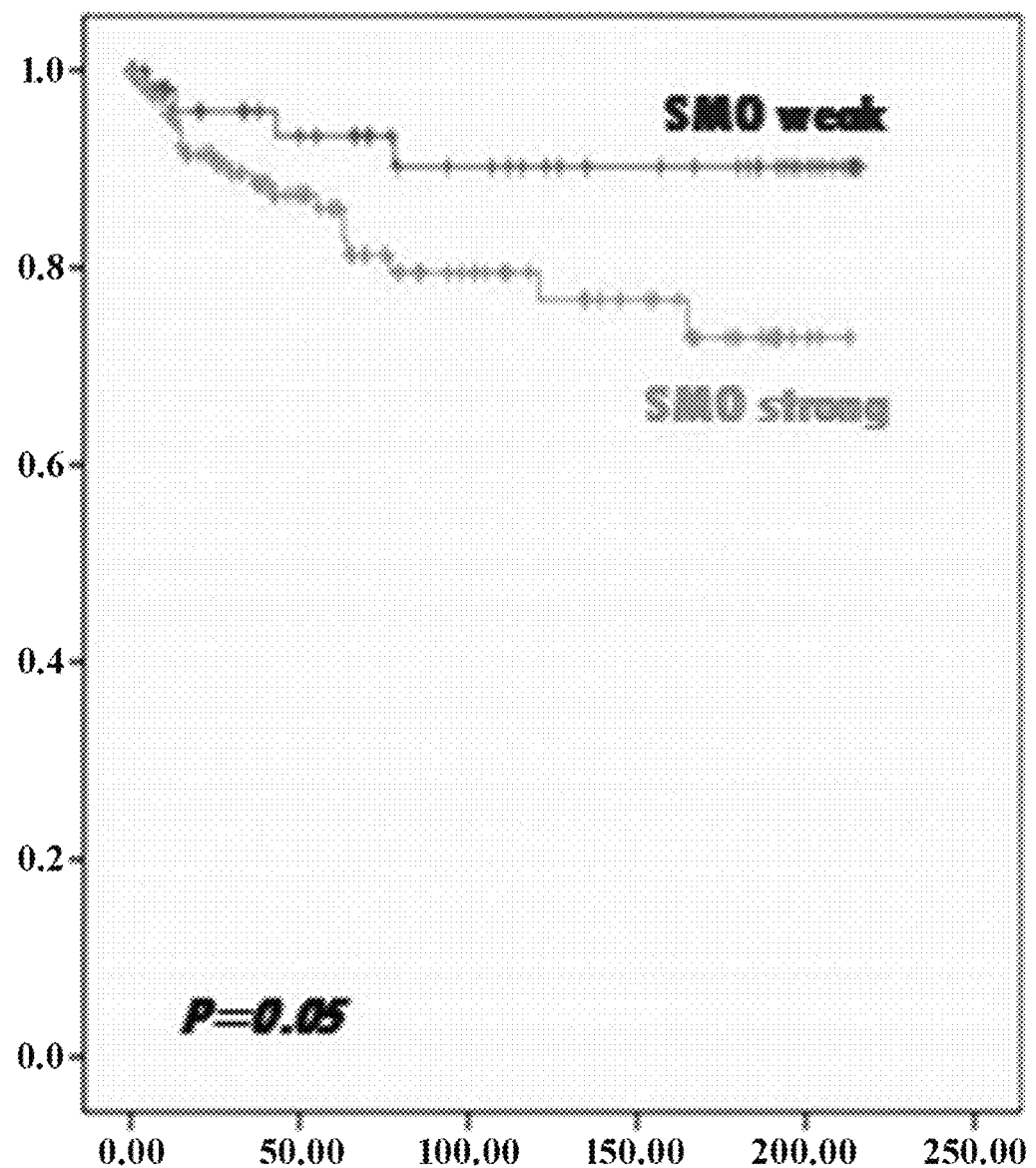
FIG. 4 shows survival curves of 206 cases of colorectal cancer tissues obtained in Example 1, which were divided into a group having low expression levels of SMO ("SMO week") and a group having high expression levels of SMO ("SMO strong").

FIG. 4 shows the survival curves of the 206 cases of colorectal cancer tissues obtained in Example 1, which were divided into a group having low expression levels of SMO ("SMO week") and a group having high expression levels of SMO ("SMO strong").

As shown in FIG. 4, the group having high expression levels of SMO (SMO strong) showed worse prognosis than the group having low expression levels of SMO (SMO week). There was a statistically significant difference (p=0.05) in the overall survival between the two groups.

<Example 3> Western Blotting for Normal and Colorectal Cancer Tissues

1. Subjects

Out of the 206 cases of colorectal cancer tissues and the 27 cases of normal tissues obtained in Example 1, 16 colorectal cancer tissues and 16 normal tissues (#1, #2, #3, #4, #5, #6, #7, #10, #21, #22, #27, #28, and #30) were selected as final subjects. Immediately after collection, the subjects were placed in liquid nitrogen for rapid freezing and stored in a freezer at −80° C. The subjects were thawed for protein isolation before the experiment.

2. Protein Isolation

Tissues were disrupted by a combination of mechanical homogenization and sonication in a lysis buffer (7 M urea, 2 M thiourea, 4% CHAPS, 40 mM Tris, 100 mM DTT) supplemented with protease, followed by centrifugation at 15,000 rpm and 4° C. for 30 min. Proteins in the supernatant were quantified by ELISA using the Bradford method.

3. Western Blotting

30 μg of the proteins isolated from the collected tissues were subjected to electrophoresis, transferred to a PVDF membrane, labeled with anti-SMO antibody (abcam, MA, USA) as a primary antibody and an HRP-conjugated anti-rabbit antibody as a secondary antibody, and detected by chemiluminescence staining. The expression levels of SMO were expressed relative to actin level ("1") by the enhanced chemiluminescence (ECL) method.

Figure 5:
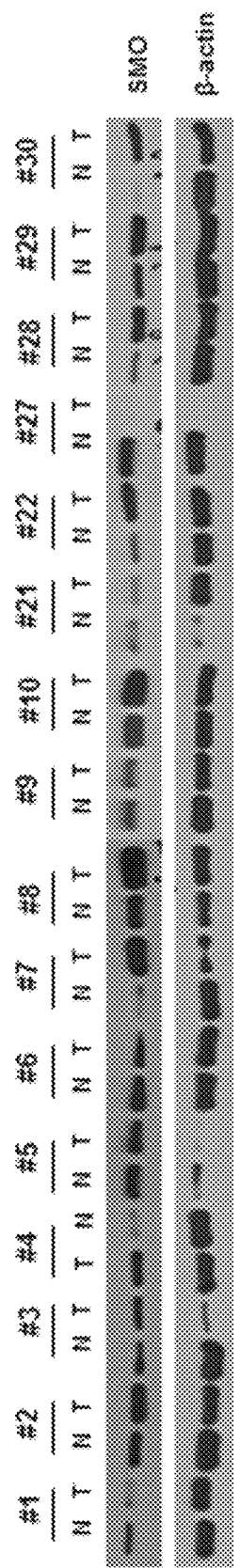
FIG. 5 shows photographic images showing the results of Western blotting for normal and colorectal cancer tissues.

In FIG. 5, the numbers succeeding # are sample numbers, and the normal and colorectal cancer tissues in each sample number are indicated by the letters N (Normal) and T (Tumor), respectively.

4. Conclusion

Figure 6:
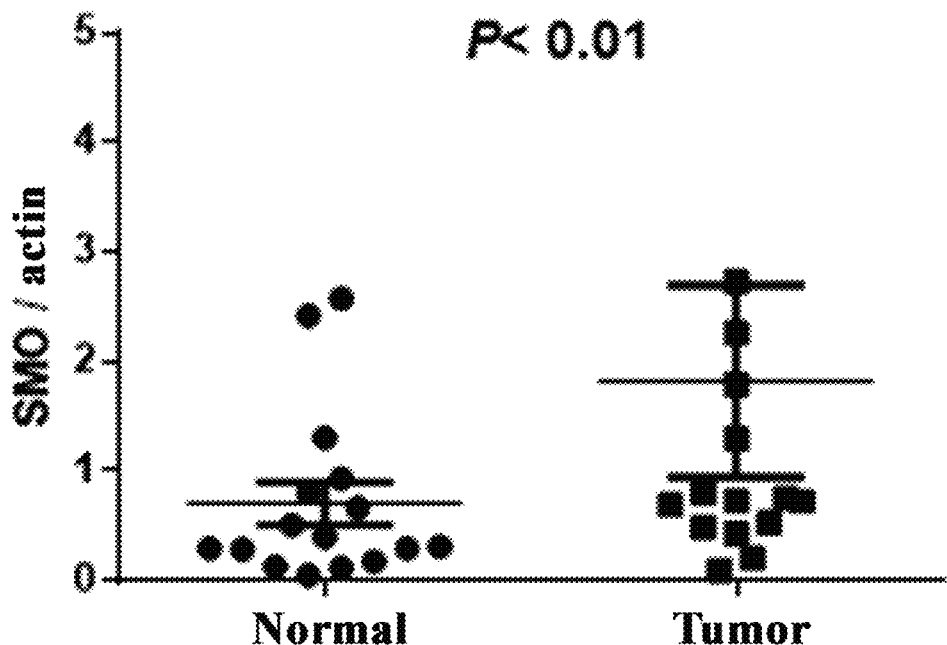
FIG. 6 shows the quantified relative SMO expressions of FIG. 5.

FIG. 5 shows photographic images showing the results of Western blotting for the normal and colorectal cancer tissues. FIG. 6 shows the quantified relative SMO expressions of FIG. 5.

As shown in FIGS. 5 and 6, the expression levels of SMO protein in the colorectal cancer tissues (Tumor: T) were higher than those in most of the normal tissues (Normal: N). There were statistically significant differences in the expression level of SMO between the normal and colorectal cancer tissues (P<0.01).

<Example 4> Analysis of Hedgehog and SMO Signaling Expressions in Various Colorectal Cancer Cell Lines 1. Colorectal cancer cell line culture Colorectal cancer cell lines (DLD-1, HCT15, HCT116, HT29, WIDR, SW48, SNUC2A, colo205, SNU283, SW480, SW620, HCT8, SNUC1, and LS174T) were purchased from the Korean Cell Line Bank. Each of the colorectal cancer cell lines was passaged three times and cultured in a 60 mm culture plate (Falcon) at a density of $1\times10^5/cm^2$. Half of the culture medium was exchanged every 3 days. A 96-well culture plate (Falcon) was used for cytotoxicity testing. RPMI 1640 supplemented with penicillin-streptomycin (100 U/ml) and 10% fetal bovine serum was used as the culture medium. Culture was performed in a humidified 5% $CO_2$ incubator (Forma, USA).

2. Western Blotting

The expression levels of GLI1, GLI2, GLI3, SHH, SMO, PTCH1, and SUFU proteins as hedgehog signaling components were investigated. To this end, each of the colorectal cancer cell lines was lysed in PRO-PREP protein extraction solution (Intron Biotechnology, Seoul, Korea). Then, proteins were extracted and quantified by BCA (Thermo Scientific, Rockford, IL, USA) before use. The proteins were separated by SDS-PAGE electrophoresis, transferred to a PVDF membrane (Millipore, Billerica, MA, USA), and blocked with 5% skim-milk. Thereafter, the blocked proteins were labeled with GLI1, GLI2, GLI3, SHH, SMO, PTCH1, SUFU antibodies and β-actin (Santa Cruz, CA, USA) at 4° C. overnight. On the next day, the proteins were washed with TBST, labeled with a goat anti-mouse IgG-HRP (Santa Cruz) at room temperature for 1 h. The expression levels of the proteins were determined using an ECL detection reagent (Bionote, Hwaseong, Korea).

3. Conclusion

Figure 7:
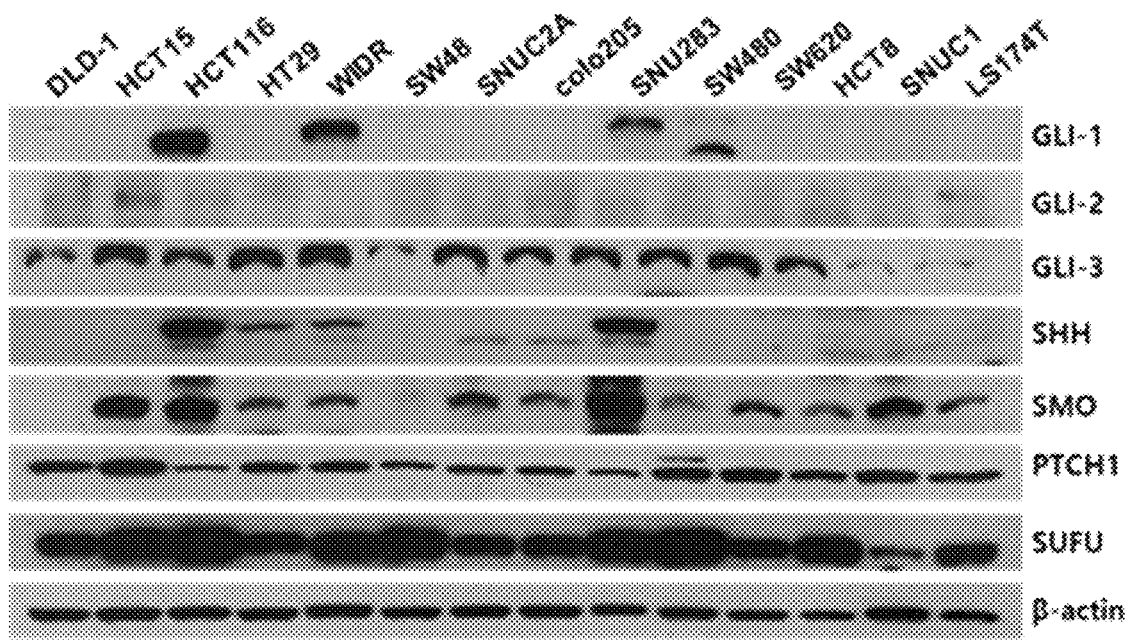
FIG. 7 shows the results of Western blotting for 14 colorectal cancer cell lines to analyze the expression levels of hedgehog signaling components GLI1, GLI2, GLI3, SHH, SMO, PTCH1, and SUFU proteins.

FIG. 7 shows the results of Western blotting for 14 colorectal cancer cell lines to analyze the expression levels of hedgehog signaling components GLI1, GLI2, GLI3, SHH, SMO, PTCH1, and SUFU proteins. As shown in FIG. 7, different protein expression profiles were observed for the colorectal cells. Particularly, the SMO and GLI1 proteins had high expression profiles in HCT116, SNU283, and SW620 cells and low expression profiles in DLD-1.

<Example 5> Analysis of Binding Abilities of SMO Antibodies in Colorectal Cancer Cell Line GCT116

1. HCT116 Colorectal Cancer Cell Line Culture

HCT116 colorectal cancer cell line was purchased from the Korean Cell Line Bank. The colorectal cancer cell line was passaged three times and cultured in a 60 mm 96-well culture plate (Falcon) at a density of $1\times10^5/cm^2$. Half of the culture medium was exchanged every 3 days. RPMI 1640 supplemented with penicillin-streptomycin (100 U/ml) and 10% fetal bovine serum was used as the culture medium. Culture was performed in a humidified 5% $CO_2$ incubator (Forma, USA) for 24 h.

2. Flow Cytometry

After completion of the culture, cells were detached by treatment with 0.05% trypsin for several minutes, collected, and washed twice with PBS. The washed cells were fixed in 3.7% formaldehyde, added with a mouse SMO antibody as a primary antibody and an Abcam SMO antibody (positive control), and left standing at 4° C. overnight. Then, the cells were washed three times with PBS, stained with an Alexa 594-conjugated secondary antibody, and analyzed by flow cytometry.

3. Conclusion

Figure 8:
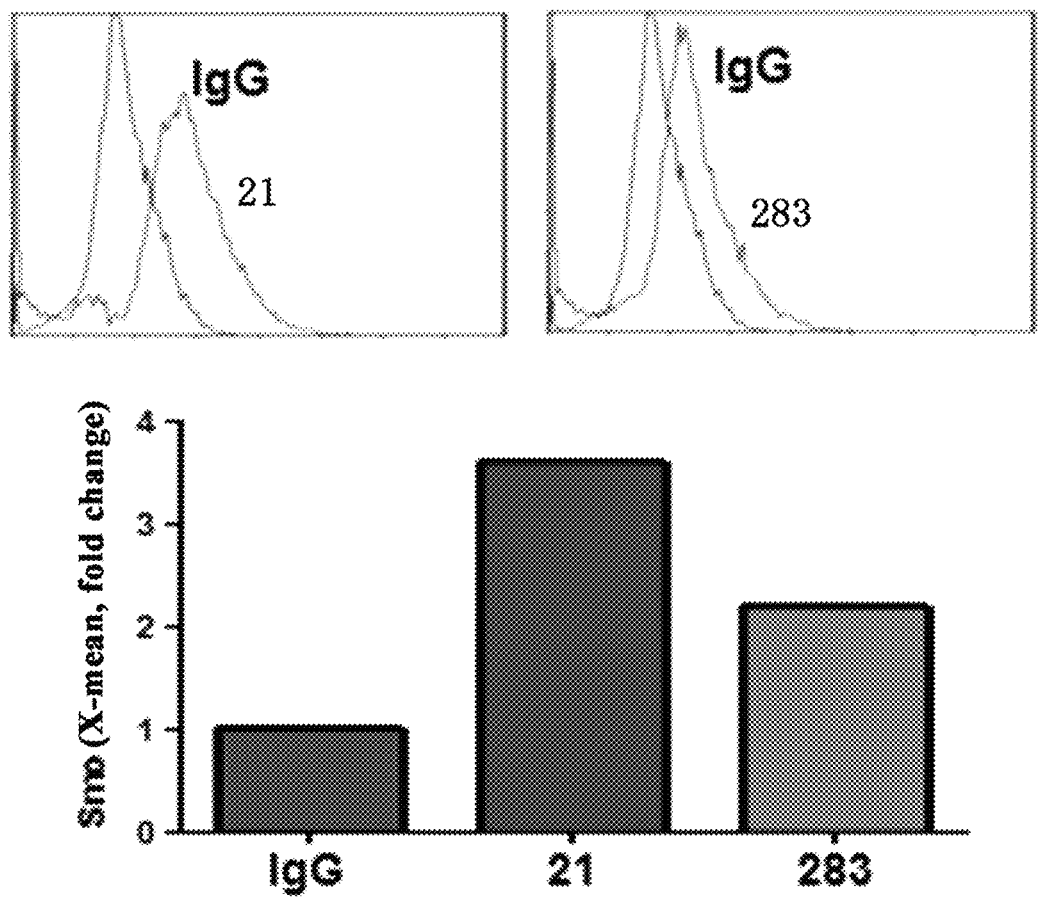
FIG. 8 shows the results of flow cytometry to determine the binding abilities of antibody No. 21 (Production Example 1) and antibody No. 283 (Production Example 2) in colorectal cancer cells HCT116. The bottom graph shows the average fluorescence intensities of the antibodies in HCT116 cells, which were measured by flow cytometry.

FIG. 8 shows the results of flow cytometry to determine the binding abilities of antibody No. 21 (Production Example 1) and antibody No. 283 (Production Example 2) in colorectal cancer cells HCT116. In FIG. 8, the bottom graph shows the average fluorescence intensities of the antibodies in HCT116 cells, which were measured by flow cytometry.

Figure 9:
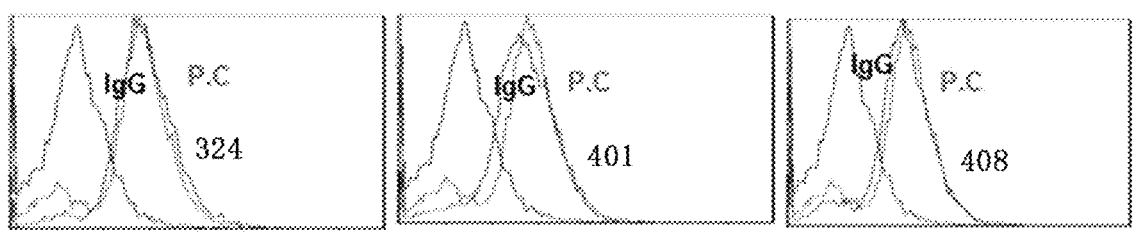
FIG. 9 shows the results of flow cytometry to determine the binding abilities of antibody No. 324 (Production Example 3), antibody No. 401 (Production Example 4), and antibody No. 408 (Production Example 5) in colorectal cancer cells HCT116. The bottom graph shows the average fluorescence intensities of the antibodies in HCT116 cells, which were measured by flow cytometry.
Figure 9:
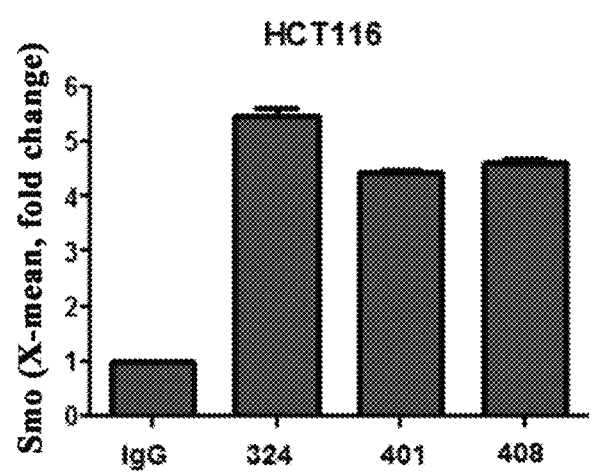

FIG. 9 shows the results of flow cytometry to determine the binding abilities of antibody No. 324 (Production Example 3), antibody No. 401 (Production Example 4), and antibody No. 408 (Production Example 5) in colorectal cancer cells HCT116. In FIG. 9, the bottom graph shows the average fluorescence intensities of the antibodies in HCT116 cells, which were measured by flow cytometry.

As shown in FIGS. 8 and 9, the binding abilities of the SMO antibodies were analyzed in the HCT116 cell line where the expressions of SMO and GLI1 were relatively high, and as a result, antibody No. 21 (Production Example 1) and antibody No. 283 (Production Example 2) were specifically bound to SMO protein in the cell line. Specifically, the ability of antibody No. 21 (Production Example 1) to bind to SMO protein was greater than that of antibody No. 283 (Production Example 2).

Antibody No. 324 (Production Example 3), antibody No. 401 (Production Example 4), and antibody No. 408 (Production Example 5) were found to effectively and specifically bind to SMO protein expressed in HCT116.

<Example 6> Determination of Binding Abilities of Mouse SMO Antibodies in Colorectal Cancer Cell Lines SW620 Con shRNA and SW620 SMO shRNA 1. Sw620 Con shRNA (Con shRNA) Preparation and Culture After SW620 cells were infected with con shRNA Lentivirus particles (santacruz, MA, USA), 1000 cells were seeded in a 100 mm dish and cultured for at least a week. SMO shRNA stable cells were acquired by colony selection with puromycin dihydrochloride and were identified by Western blotting.

In this experimental example, culture was performed for 24 h.

2. SW620 SMO shRNA (SMO shRNA) Preparation and Culture

After SW620 cells were infected with SMO shRNA Lentivirus particles (santacruz, LS-40161-V, MA, USA), 1000 cells were seeded in a 100 mm dish and cultured for at least a week. SMO shRNA stable cells were acquired by colony selection with puromycin dihydrochloride and were identified by Western blotting. A knock-down colony was selected and used.

In this experimental example, culture was performed for 24 h.

3. Flow Cytometry

After completion of the culture (24 h), cells were detached by treatment with 0.05% trypsin for several minutes, collected, and washed twice with PBS. The washed cells were fixed in 3.7% formaldehyde, added with a mouse SMO antibody as a primary antibody and an Abcam SMO antibody (positive control), and left standing at 4° C. overnight. Then, the cells were washed three times with PBS, stained with an Alexa 594-conjugated secondary antibody, and analyzed by flow cytometry.

4. Conclusion

Figure 10:
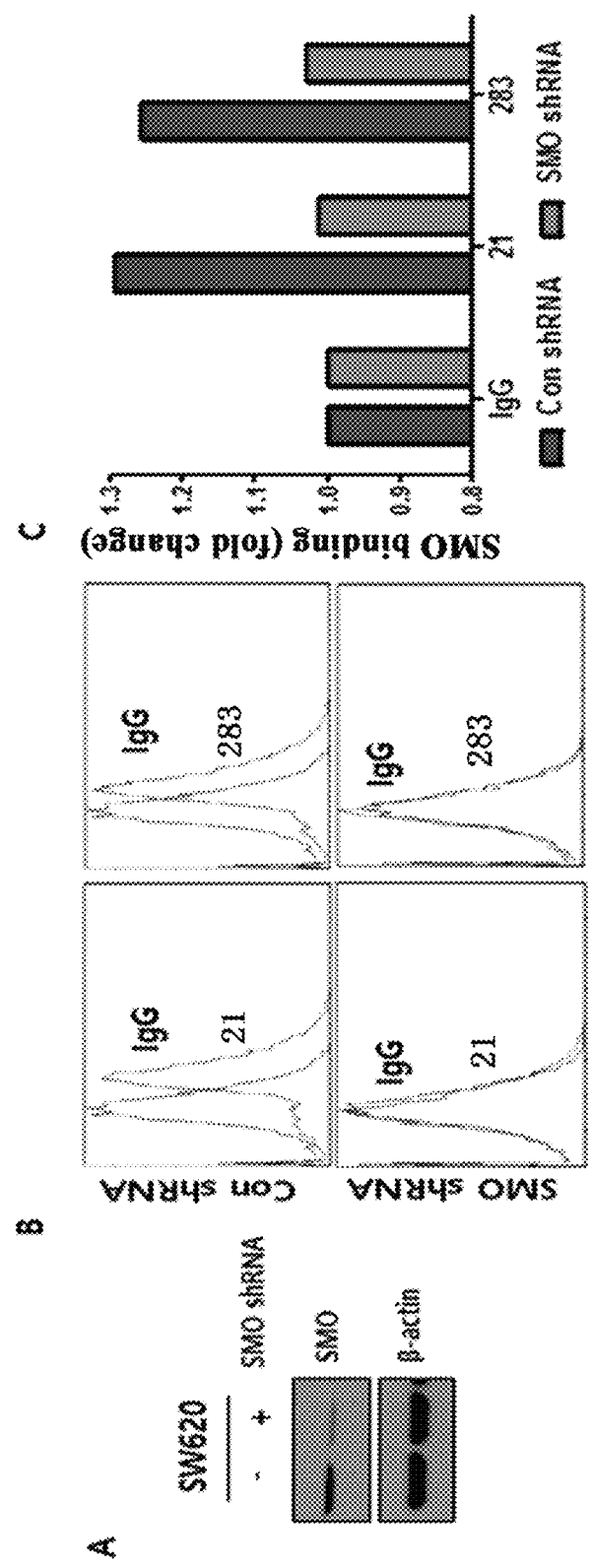
FIG. 10 shows (A) the results of Western blotting for SW620 con shRNA and SW620 SMO shRNA cells, (B) the results of flow cytometry to determine the binding abilities of antibody No. 21 (Production Example 1) and antibody No. 283 (Production Example 2) in SW620 con shRNA and SW620 SMO shRNA cells, and (C) the average fluorescence intensities of the antibodies in HCT116 cells, which were measured by flow cytometry in FIG. 10B.

FIG. 10 shows (A) the results of Western blotting for SW620 con shRNA and SW620 SMO shRNA cells, (B) the results of flow cytometry to determine the binding abilities of antibody No. 21 (Production Example 1) and antibody No. 283 (Production Example 2) in SW620 con shRNA and SW620 SMO shRNA cells, and (C) the average fluorescence intensities of the antibodies in HCT116 cells, which were measured by flow cytometry in FIG. 10B.

SMO-expressing colorectal cancer cell line SW620 was treated with shRNA to prepare cells with reduced expression of SMO, which were treated with the antibodies (Production Examples 1 and 2) to determine whether the SMO antibodies were capable of binding to SMO protein. As shown in FIG. 10, when the SMO shRNA cells with reduced expression of SMO protein were treated with antibody No. 21 (Production Example 1) and antibody No. 283 (Production Example 2), no binding of the antibodies to SMO protein was observed. In contrast, increased binding of the antibodies to SMO protein was observed in Con shRNA, demonstrating the ability of the SMO antibodies to specifically bind to SMO protein.

<Example 7> Determination of Competitive SMO Binding Abilities Using BODIPY-Cyclopamine in Colorectal Cancer Cell Line HCT116

1. HCT116 Colorectal Cancer Cell Line Culture

HCT116 colorectal cancer cell line was purchased from the Korean Cell Line Bank. The colorectal cancer cell line was passaged three times and cultured in a 60 mm culture plate (Falcon) at a density of $1 \times 10^5/cm^2$. Half of the culture medium was exchanged every 3 days. RPMI 1640 supplemented with penicillin-streptomycin (100 U/ml) and 10% fetal bovine serum was used as the culture medium. Culture was performed in a humidified 5% $CO_2$ incubator (Forma, USA) for 24 h.

2. In Vitro Competition of the Inventive SMO Antibody and BODIPY-Cyclopamine (BC)

This experiment was conducted according to the protocol described in Roudaut et al., Mol. Pharmacol. 79: 453-460, 2011. Specifically, cells were cultured with the inventive SMO antibody (Production Example 1 or 2) for 24 h in the presence or absence of BC (10 nM) for 2 h. After the culture was finished, cells were fixed in 3.7% formaldehyde and cell nuclei were visualized by blue DAPI staining. Next, cells were mounted and observed by confocal microscopy for the production of reactive oxygen species.

The inhibition of the binding of BODIPY-cyclopamine (BC) by the SMO antibody (Production Example 1 or 2) was measured by the decrease in fluorescence photographed and quantified using the PCI 6.2 software (Hamamatsu Corporation), then referred to the surface area of the nuclei present on the photograph.

3. Conclusion

Figure 11:
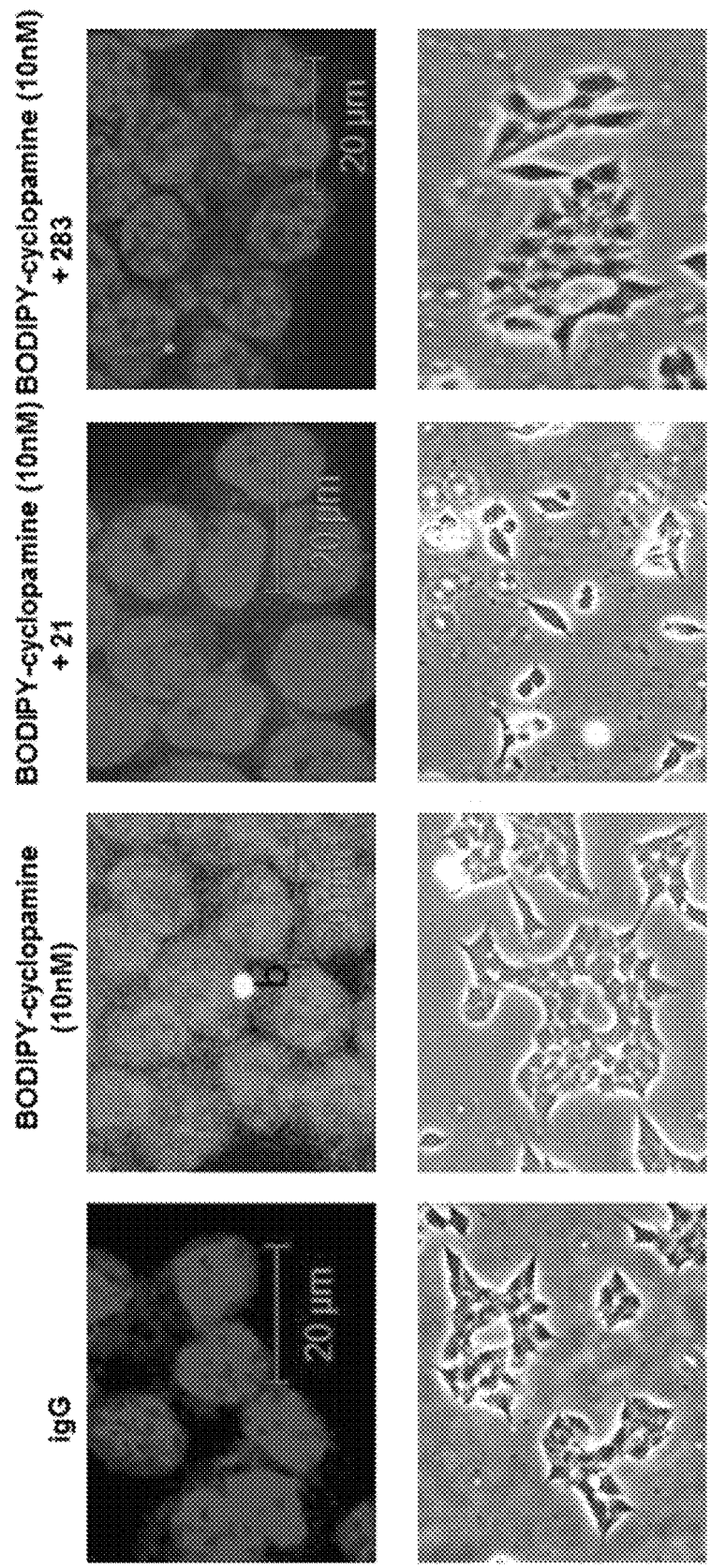
FIG. 11 shows confocal microscopy images after simultaneous treatment with BODIPY-cyclopamine (BC) and an inventive SMO antibody to analyze in vitro competitive binding abilities of the SMO antibody and BC.

FIG. 11 shows confocal microscopy images after simultaneous treatment with BODIPY-cyclopamine (BC) and the inventive SMO antibody to analyze in vitro competitive binding abilities of the SMO antibody and BC.

After simultaneous treatment with BODIPY-cyclopamine (green) and antibody No. 21 (Production Example 1) or antibody No. 283 (Production Example 2), an observation was made as to whether or not the inventive antibody competed with BODIPY-cyclopamine for binding to SMO protein in colorectal cancer cell line HCT116.

As shown in FIG. 11, when BODIPY-cyclopamine was treated alone in HCT116 cells untreated with the inventive SMO antibody, BODIPY-cyclopamine was well bound to SMO protein in the cells, which was explained by an increase in green color. In contrast, when cells were simultaneously treated with BODIPY-cyclopamine and antibody No. 21 or antibody No. 283, the binding of BODIPY-cyclopamine (BC) was inhibited by the inventive SMO antibody (Production Example 1 or 2), which was explained by a reduction in green fluorescence intensity. These results lead to the conclusion that antibody No. 21 and antibody No. 283 have high affinities for SMO protein in cells.

<Example 8> Determination of Inhibitory Activity of Mouse SMO Antibodies on GLI 1. NIH3T3-GLI Cell Line Culture Gli Repoter-NIH3T3 cell line was purchased from BPS Bioscience (CA, USA).

2. NIH3T3-GLI Reporter Assay 24 h after NIH3T3-GLI cells having GLI transcriptional activity were plated in a 96-well plate at a density of $1\times10^4$ cells/cm$^2$, the cells were treated with Sonic hedgehog peptide for 30 min. Next, the cells were treated with antibody No. 21 or 283 for 24 h and GLI1 Reporter activity (%) was measured through luminescence using a Reporter assay kit (Promega, WI, USA). The above procedure was repeated except that the SMO small-molecule inhibitor vismodegib or erismodegib was used as a positive control instead of the inventive SMO antibody.

3. Conclusion

Figure 12:
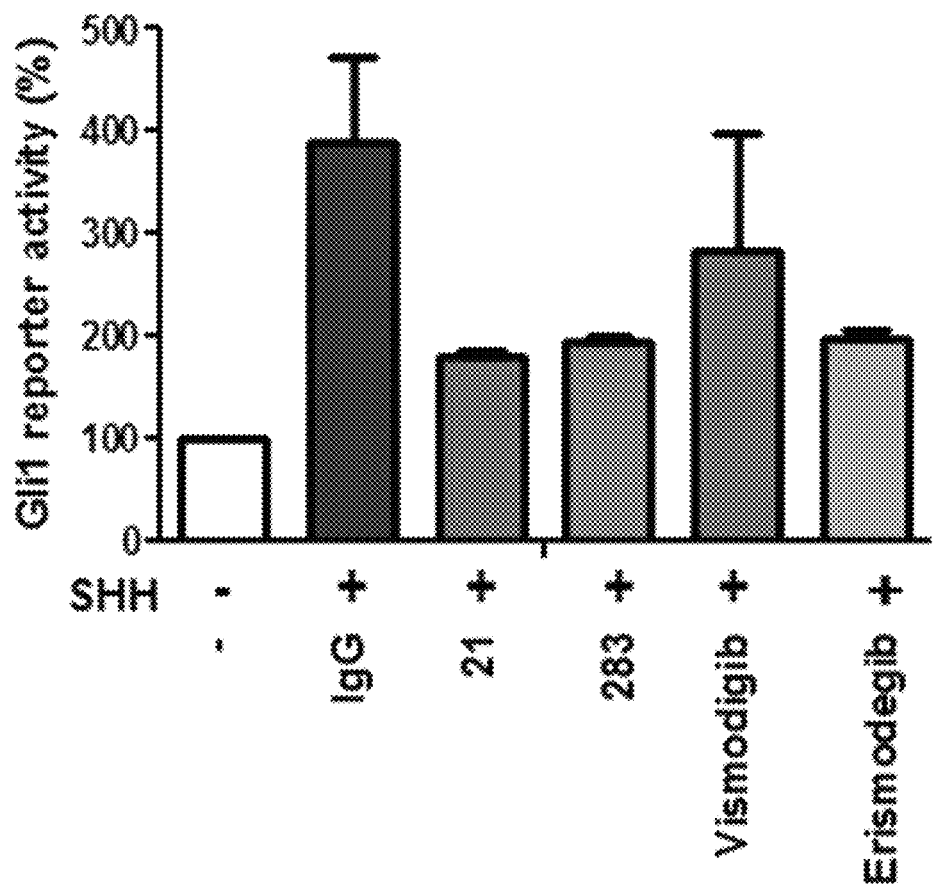
FIG. 12 shows the Gill reporter activities (%) of antibodies in NIH3T3-GLI cells.

FIG. 12 shows the Gill reporter activities (%) of the inventive SMO antibodies in NIH3T3-GLI cells. Specifically, GLI is a downstream signaling component in the hedgehog signaling pathway and Gill Reporter activities were analyzed from NIH3T3-GLI cells treated with different substances to determine the transcriptional regulation ability of GLI. As a result, it was found that the use of the inventive antibodies (antibody No. 21 and antibody No. 283) significantly inhibited the transcriptional activity of GLI than the positive control treated with vismodegib or erismodegib. The Gill Reporter activities of the inventive SMO antibodies numerically at least 2 times lower than that of the negative control group (IgG) and 1.5 times lower than or similar to those of the conventional SMO small-molecule inhibitors.

The inventive SMO antibodies were confirmed to effectively inhibit the SHH-induced GLI transcriptional activity, revealing that treatment of the SMO antibodies in a cell line where SMO expression is high can inhibit cell growth. In conclusion, the use of the inventive SMO antibodies is expected to be useful for personalized treatment.

<Example 9> Determination of Inhibitory Activities of Mouse SMO Antibodies on Cell Growth on in Colorectal Cancer Cell Lines 1. Culture of Normal Colorectal Cells and Colorectal Cancer Cell Lines CCD-18Co (normal colorectal cells), HCT116, DLD-1, HCT16, Colo205, and SW620 cells were purchased from the Korean Cell Line Bank. Each of the cell lines was passaged three times and cultured in a 60 mm 96-well culture plate (Falcon) at a density of $1\times10^5$/cm$^2$. Half of the culture medium was exchanged every 3 days. RPMI 1640 supplemented with penicillin-streptomycin (100 U/ml) and 10% fetal bovine serum was used as the culture medium. Culture was performed in a humidified 5% CO$_2$ incubator (Forma, USA) for 24 h.

2. SW620 (conshRNA) and SW620 (SMOshRNA) Cell Preparation and Culture

SW620 (conshRNA) cells were prepared and cultured as follows. After SW620 cells were infected with con shRNA Lentivirus particles (santacruz, MA, USA), 1000 cells were seeded in a 100 mm dish and cultured for at least a week. SMO shRNA stable cells were acquired by colony selection with puromycin dihydrochloride and were identified by Western blotting. In this experimental example, culture was performed for 24 h.

SW620 (SMOshRNA) cells were prepared and cultured as follows. After SW620 cells were infected with SMO shRNA Lentivirus particles (santacruz, LS-40161-V, MA, USA), 1000 cells were seeded in a 100 mm dish and cultured for at least a week. SMO shRNA stable cells were acquired by colony selection with puromycin dihydrochloride and were identified by Western blotting. A knock-down colony was selected and used. In this experimental example, culture was performed for 24 h.

3. Western Blotting

Each of the cell lines was lysed in PRO-PREP protein extraction solution (Intron Biotechnology, Seoul, Korea). Then, proteins were extracted and quantified by BCA (Thermo Scientific, Rockford, IL, USA) before use. The proteins were separated by SDS-PAGE electrophoresis, transferred to a PVDF membrane (Millipore, Billerica, MA, USA), and blocked with 5% skim-milk. Thereafter, the blocked proteins were labeled with the inventive SMO antibodies and β-actin (Santa Cruz, CA, USA) at 4° C. overnight. On the next day, the proteins were washed with TBST, labeled with a goat anti-mouse IgG-HRP (Santa Cruz) at room temperature for 1 h. The expression levels of the proteins were determined using an ECL detection reagent (Bionote, Hwaseong, Korea).

4. WST-1 Assay 24 h after the colorectal cancer cells and the normal cells were plated in 96-well plates, different concentrations (0 and 10 μg/ml) of antibody No. 21 (Production Example 1) and antibody No. 283 (Production Example 2) were added to the well plates. Following 24 h, the cells were incubated with WST-1 solution for 4 h and cell viability was assessed by measuring absorbance at 450 nm.

5. Conclusion

Figure 13:
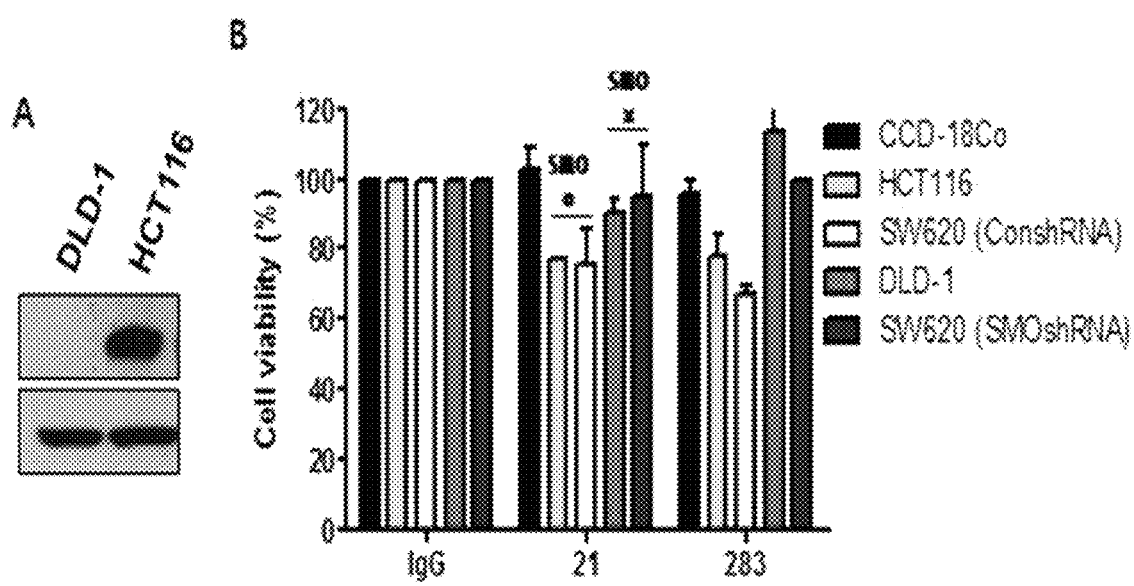
FIG. 13 shows (A) the expressions of SMO in normal and colorectal cancer cells and (B) the viabilities of the cells after treatment with antibody No. 21 (Production Example 1) and antibody No. 283 (Production Example 2), which were measured by Western blotting and WST-1 assay, respectively.

FIG. 13 shows (A) the expressions of SMO in normal and colorectal cancer cells and (B) the viabilities of the cells after treatment with antibody No. 21 (Production Example 1) and antibody No. 283 (Production Example 2), which were measured by Western blotting and WST-1 assay, respectively.

As shown in FIG. 13, there was no substantial change in the growth of the normal colorectal cells CCD-18Co regardless of the presence or absence of the inventive SMO antibody. In contrast, the treatment with antibody No. 21 and antibody No. 283 in HCT116 and SW620 con shRNA cells expressing SMO protein inhibited cell growth. That is, changes in the growth of DLD-1 and SW620 SMO shRNA cells, where the expressions of SMO protein were relatively low, depending on the presence or absence of the SMO antibody were insignificant. In conclusion, the inventive SMO antibodies have specific inhibitory activities on the growth of colorectal cancer cells.

Figure 14:
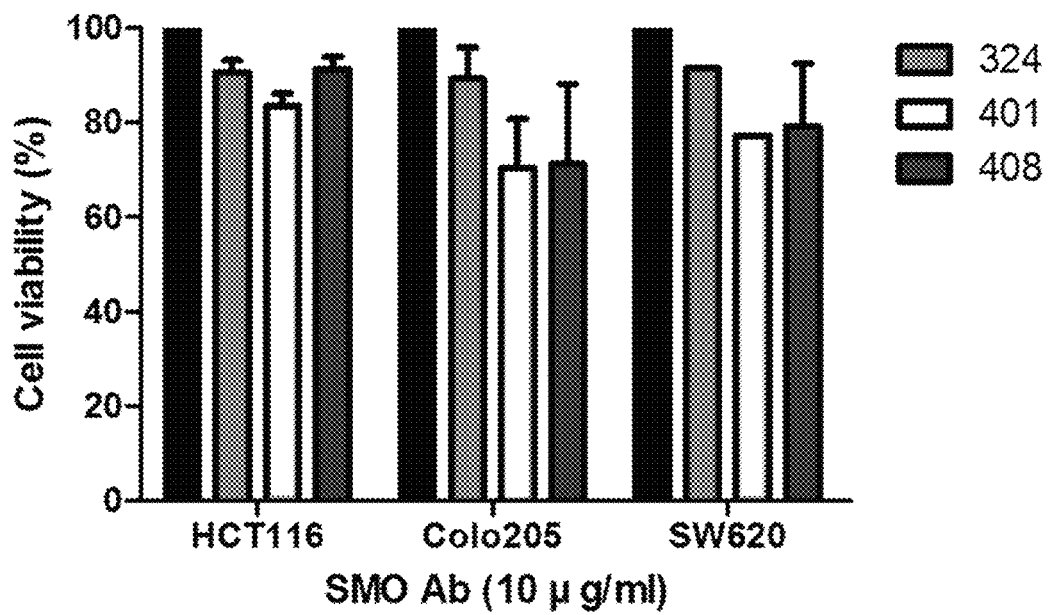
FIG. 14 shows the viabilities of colorectal cancer cells after treatment with antibody No. 324 (Production Example 3), antibody No1. 401 (Production Example 4), and antibody No. 408 (Production Example 5), which were measured by WST-1 assay.

FIG. 14 shows the viabilities of colorectal cancer cells after treatment with antibody No. 324 (Production Example 3), antibody Nol. 401 (Production Example 4), and antibody No. 408 (Production Example 5), which were measured by WST-1 assay. As shown in FIG. 14, the addition of the SMO antibodies (Production Examples 3-5) to colorectal cancer cell line HCT16 and Colo205 and SW620 cells was confirmed to inhibit cell growth. Specifically, the SMO antibody (Production Example 3) was verified to be much more effective in inhibiting cell growth than the SMO antibody (Production Example 4 or 5).

<Example 10> Determination of Inhibitory Activities of the Mouse SMO Antibodies on Cell Growth in Colorectal Cancer Cell Lines Using 3D Culture 1. Analysis of Role of the SMO Antibodies Through 3D Culture Colo205, HCT116, and SW620 colorectal cancer cells were plated in 96-well plates for 3D culture at a density of $1 \times 10^4$ cells/cm$^2$ and cultured for 72 h. Cells were treated with 10 μg/ml of one of the SMO antibodies (Examples 1 to 5). After culture for 3-4 days, WST-1 solution was added, followed by incubation for 4 h. Cell survival (%) was assessed by measuring absorbance at 450 nm.

2. Conclusion

Figure 15:
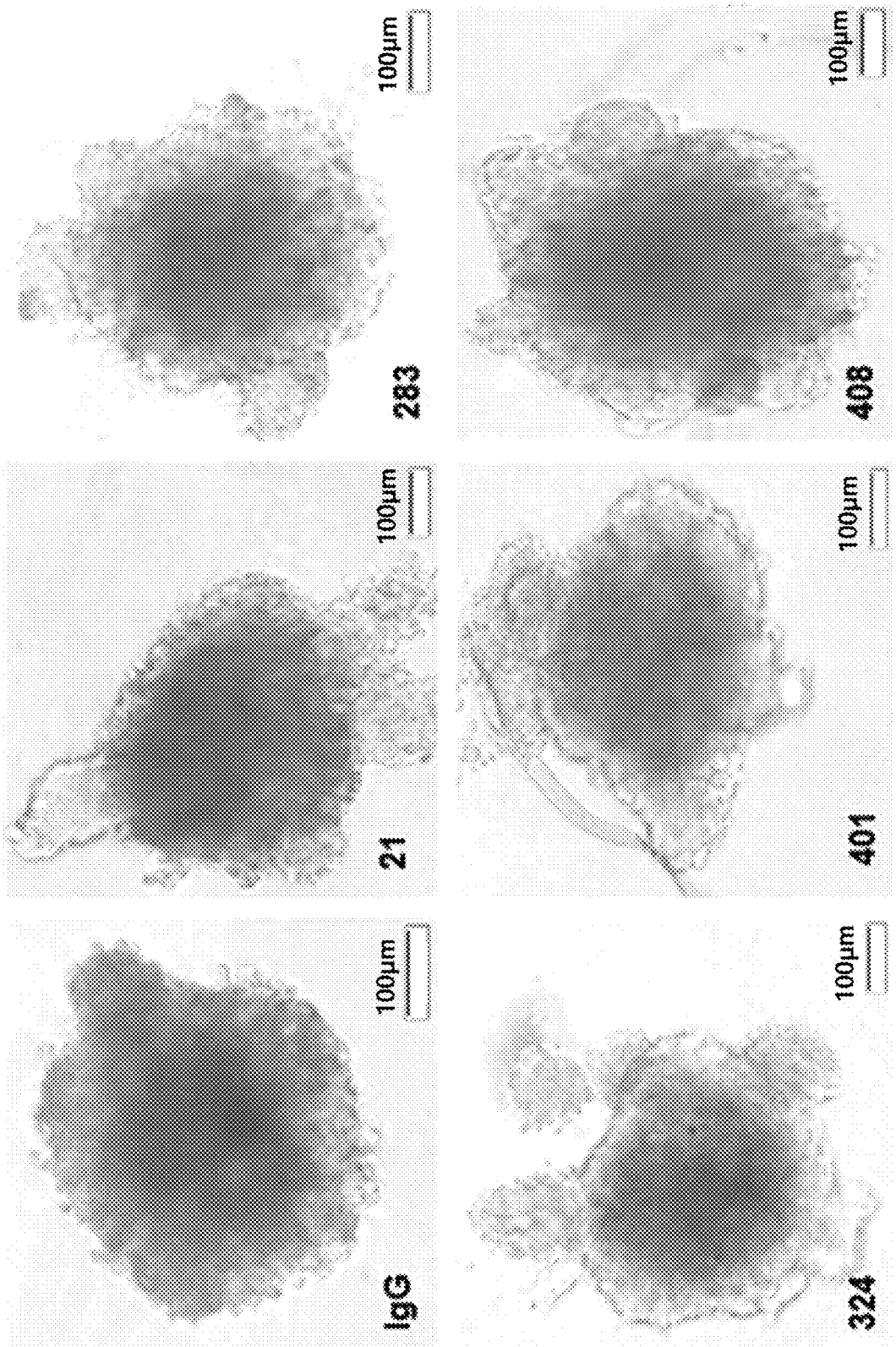
FIG. 15 shows images of HCT116 cells treated with SMO antibodies (Production Examples 1-5) in 3D culture systems to determine the inhibitory activities of the antibodies on cell growth.
Figure 16:
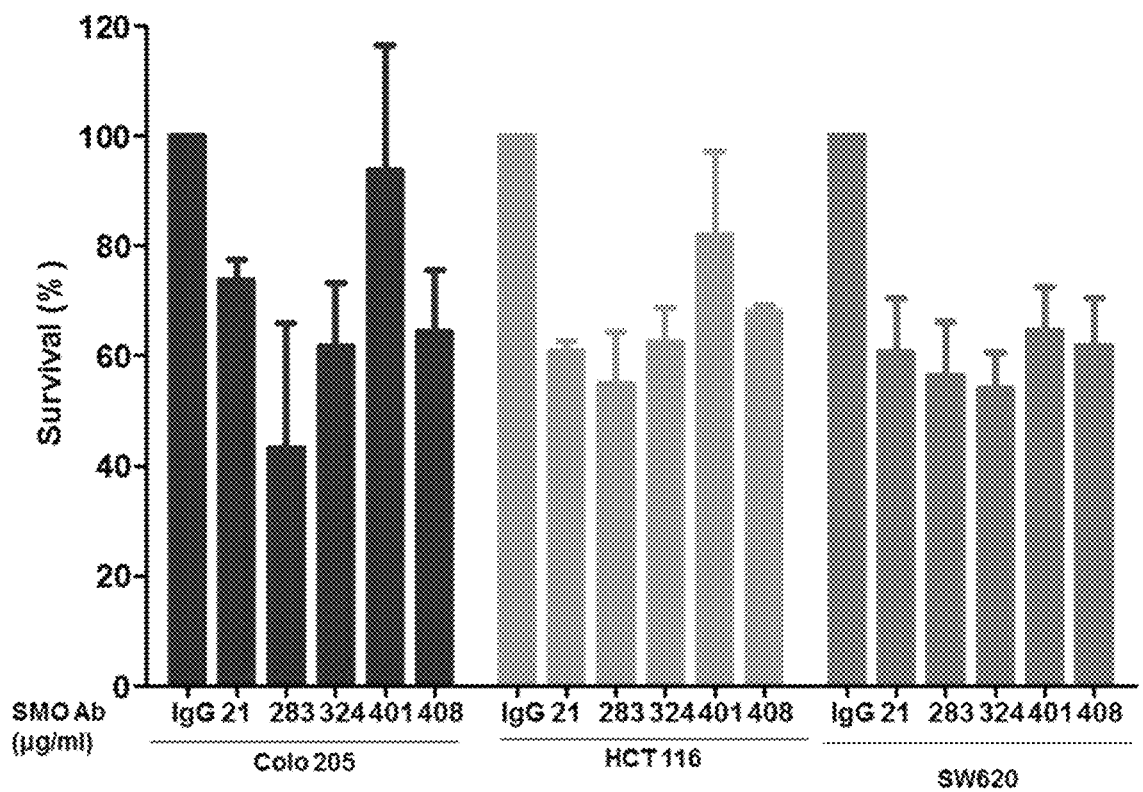
FIG. 16 shows the inhibitory activities of antibodies (Production Examples 1-5) on the growth of different colorectal cancer cells after treatment with the antibodies, which were determined by WST-1 assay.

FIG. 15 shows images of HCT116 cells treated with the SMO antibodies (Production Examples 1-5) in 3D culture systems to determine the inhibitory activities of the antibodies on cell growth. FIG. 16 shows the inhibitory activities of the antibodies (Production Examples 1-5) on the growth of different colorectal cancer cells after treatment with the antibodies, which were determined by WST-1 assay.

As shown in FIGS. 15 and 16, the inhibitory effects of the SMO antibodies (Production Examples 1-5) on the growth of colorectal cancer cell line HCT116 and Colo205 and SW620 cells were confirmed using 3D culture systems. Specifically, the treatment of the colorectal cancer cells with the SMO antibodies (Production Examples 1-5) caused budding in the spheres. This budding leads to destruction of the cells from the outside. In contrast, the control (IgG) cells maintained their circular shape. That is, the inventive SMO antibodies were found to be highly effective in inhibiting the growth of the cancer cells without affecting the normal cells.

<Example 11> Analysis of Expression Profiles of Apoptotic Proteins in Colorectal Cancer Cells in the Presence of the Inventive SMO Antibodies 1. Colorectal Cancer Cell Line Culture HCT116 colorectal cancer cell line was purchased from the Korean Cell Line Bank. The colorectal cancer cell line was passaged three times and cultured in a 60 mm culture plate (Falcon) at a cell density of $1 \times 10^5$/cm$^2$. Half of the culture medium was exchanged every 3 days. A 96-well culture plate (Falcon) was used for cytotoxicity testing. RPMI 1640 supplemented with penicillin-streptomycin (100 U/ml) and 10% fetal bovine serum was used as the culture medium. Culture was performed in a humidified 5% $CO_2$ incubator (Forma, USA).

2. Western Blotting

A determination was made as to whether the addition of the SMO antibodies increased apoptosis of cancer cells. To this end, cleavage forms of apoptosis-related marker proteins PARP and caspase-9 were analyzed.

First, after 24-h culture, the colorectal cancer cell line was treated with various concentrations (0, 5, 10, 20 μg) of the SMO antibody (Production Example 1 or 2). Following 24 h, cells were harvested and proteins were extracted by lysis. The proteins were separated by SDS-PAGE electrophoresis, transferred to a PVDF membrane (Millipore, Billerica, MA, USA), and blocked with 5% skim-milk. Thereafter, c-PARP (cell signaling, MA, USA), c-caspase-9 antibody (cell signaling, MA, USA), and β-actin (Santa Cruz, CA, USA) were conjugated at 4° C. overnight, washed with TBST the next day, and conjugated with a goat anti-mouse IgG-HRP antibody (Santa Cruz) at room temperature for 1 h. The expression levels of the proteins were determined using an ECL detection reagent (Bionote, Hwaseong, Korea).

3. Conclusion

Figure 17:
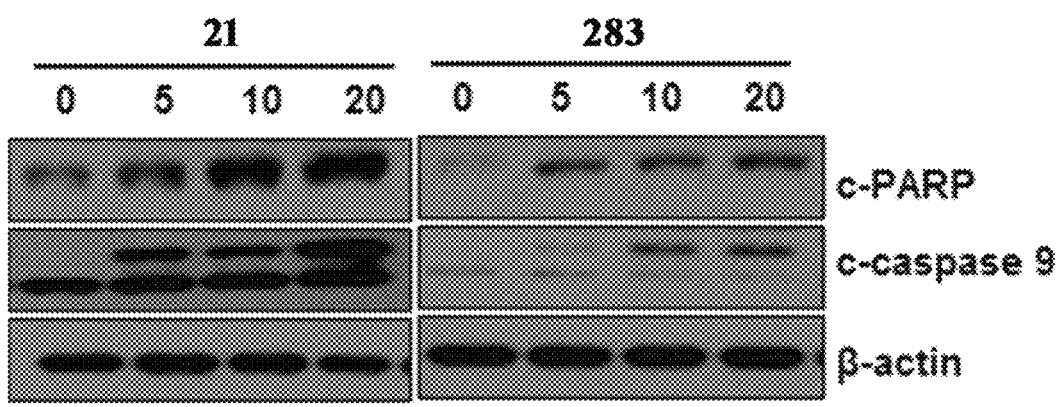
FIG. 17 shows the results of Western blotting for colorectal cancer cell line HCT116 treated with various concentrations of SMO antibodies to analyze the expressions of cleavage forms of apoptosis-related PARP and caspase-9.

FIG. 17 shows the results of Western blotting for colorectal cancer cell line HCT116 treated with various concentrations of the SMO antibodies to analyze the expressions of cleavage forms of apoptosis-related PARP and caspase-9. As shown in FIG. 17, as the concentrations of antibody No. 21 and antibody No. 283 in the colorectal cancer cell line HCT116 increased after treatment with the SMO antibodies, the expression levels of the apoptotic proteins increased. These results concluded that the inventive SMO antibodies also induce apoptosis of cancer cells.

<Example 12> Analysis of Anticancer Effects of the SMO Antibody (Production Example 1) on Oxaliplatin-Resistant Colorectal Cancer Cell Line and Cetuximab-Resistant Colorectal Cancer Cell Line 1. Culture of Oxaliplatin-Resistant Colorectal Cancer Cell Line and Cetuximab-Resistant Colorectal Cancer Cell Lines DLD-1R$^{oxa}$, an oxaliplatin-resistant colorectal cancer cell line, and SW48R$^{cet}$, a cetuximab-resistant colorectal cancer cell line, were treated with low-to-high concentrations of the anticancer drugs. The treated cell lines were cultured.

2. Analysis of Anticancer Effects (WST-1 Assay)

The oxaliplatin-resistant colorectal cancer cell line and the cetuximab-resistant colorectal cancer cell line were plated in 96-well plates, cultured for 24 h, and treated with various concentrations (0 and 10 μg/ml) of antibody No. 21 (Production Example 1). Following 24 h, the cells were incubated with WST-1 solution for 4 h and cell viability was assessed by measuring absorbance at 450 nm.

3. Conclusion

Figure 18:
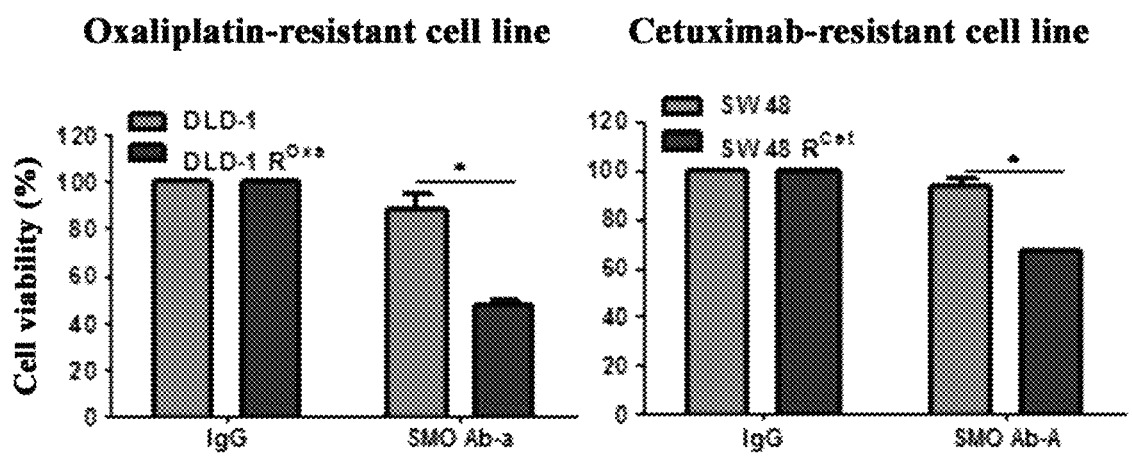
FIG. 18 shows the inhibitory activities of a SMO antibody (Production Example 1) on the growth of an oxaliplatin-resistant colorectal cancer cell line ((DLD-1R$^{oxa}$) and a cetuximab-resistant colorectal cancer cell line (SW48R$^{cet}$) after treatment with various concentrations of the SMO antibody, which were determined by WST-1 assay.

FIG. 18 shows the inhibitory activities of the SMO antibody (Production Example 1) on the growth of the oxaliplatin-resistant colorectal cancer cell line ((DLD-1R$^{oxa}$) and the cetuximab-resistant colorectal cancer cell line (SW48R cet) after treatment with various concentrations of the SMO antibody, which were determined by WST-1 assay. As shown in FIG. 18, the viabilities of the oxaliplatin-resistant colorectal cancer cell line and the cetuximab-resistant colorectal cancer cell line were significantly reduced to 40-60% when treated with antibody No. 21.

In conclusion, the inventive SMO antibody has an anticancer activity against existing drug-resistant cancer cells.

<Example 13> Analysis of Inhibitory Activity of the SMO Antibody (Production Example 1) Against Tumors in Xenograft Mouse Models Using Colorectal Cancer Cell Line HC116-Luc 1. Xenograft Animal Models In this experiment, 6-week-old BALB/c-nu/nu female mice were used as experimental animals. $1 \times 10^6$ HCT116-Luc cells were injected into the subcutaneous fat of the mice (n=6) to generate xenograft tumor animal models. Following one week, the tumor size reached 250-300 mm$^3$.

2. Experimental Procedure

First, when the tumor size of the xenograft animal models was 250-300 mm$^3$, 0 mg/kg (control), 10 mg/kg, and 20 mg/kg of the SMO antibody (Production Example 1) were directly injected into the tumor tissues once a day for 6 days. The tumor size was measured every 3 days. Following about one month, luciferase activity was measured using an in vivo imaging system. The animal models were sacrificed and tumor tissues were excised.

3. Conclusion

Figure 19:
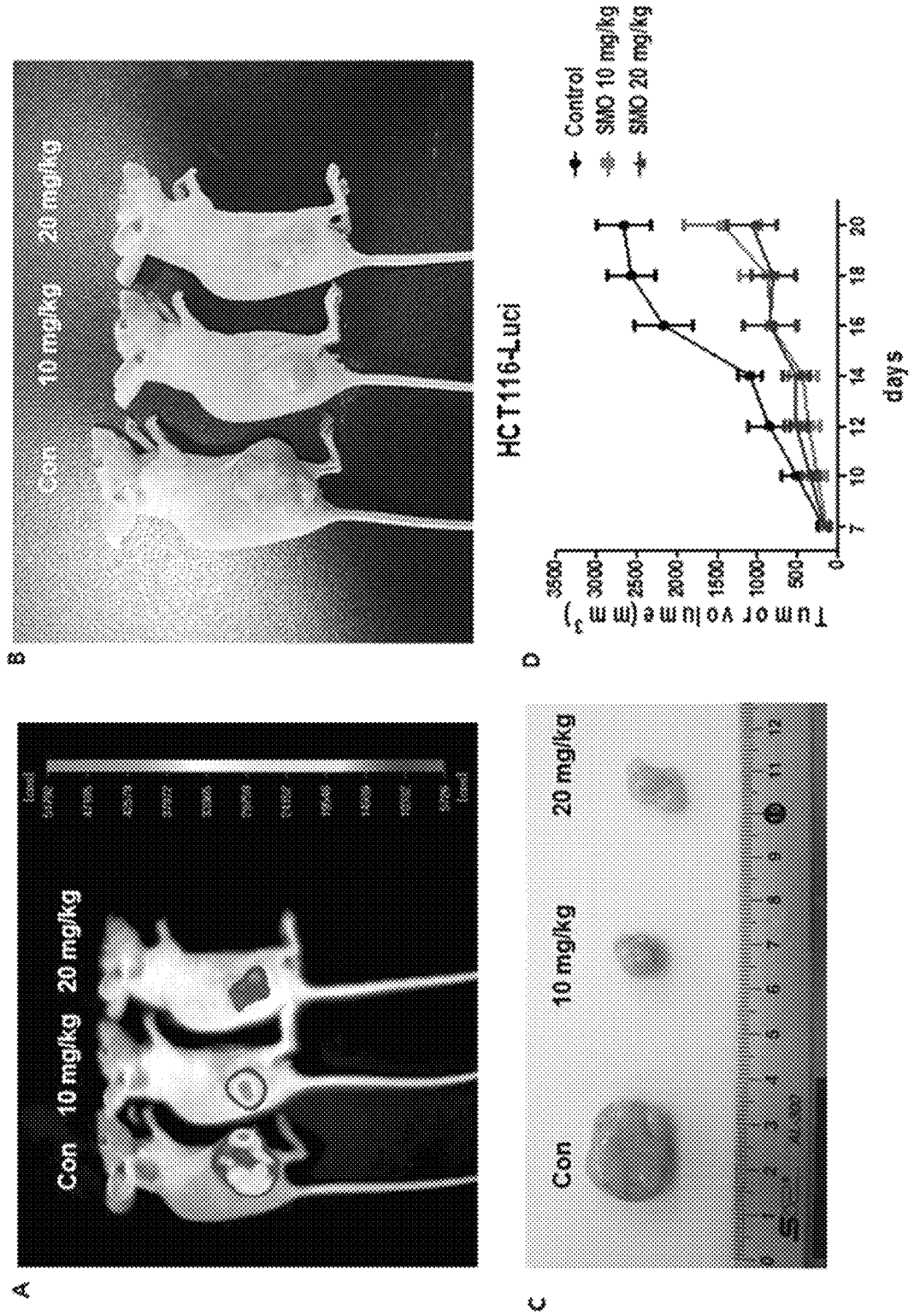
FIG. 19 shows (A) a fluorescence microscopy image of xenograft animal models administered 0 mg/kg (control), 10 mg/kg, and 20 mg/kg of a SMO antibody (Production Example 1), (B) an optical microscopy image of xenograft animal models administered 0 mg/kg (control), 10 mg/kg, and 20 mg/kg of a SMO antibody (Production Example 1), (C) a photographic image of tumor tissues excised from xenograft animal models ~1 month after administration of 0 mg/kg (control), 10 mg/kg, and 20 mg/kg of a SMO antibody (Production Example 1), and (D) time-dependent changes in the volume of tumors in xenograft animal models.

FIG. 19 shows (A) a fluorescence microscopy image of the xenograft animal models administered 0 mg/kg (control), 10 mg/kg, and 20 mg/kg of the SMO antibody (Production Example 1), (B) an optical microscopy image of the xenograft animal models administered 0 mg/kg (control), 10 mg/kg, and 20 mg/kg of the SMO antibody (Production Example 1), (C) a photographic image of the tumor tissues excised from the xenograft animal models ~1 month after administration of 0 mg/kg (control), 10 mg/kg, and 20 mg/kg of the SMO antibody (Production Example 1), and (D) time-dependent changes in the volume of tumors in the xenograft animal models.

As shown in FIG. 19, the tumor size in the xenograft animal models was reduced to less than half of that in the control group by administration of 10 mg/kg and 20 mg/kg of the SMO antibody (Production Example 1). In conclusion, the inventive SMO antibody is substantially effective in inhibiting tumor growth and metastasis.

<Example 14> Determination of Inhibitory Activities of the Humanized SMO Antibodies Against GLI 1. NIH3T3-GLI Cell Line Culture GLI Repoter-NIH3T3 cell line was purchased from BPS Bioscience (CA, USA).

2. NIH3T3-GLI Reporter Assay

After NIH3T3-GLI cells having GLI transcriptional activity were plated in a 96-well plate at a density of $1\times10^4$ cells/cm$^2$, 2% BCS was treated with Sonic hedgehog peptide. Following 15 h, the cells were treated with different concentrations (10 and 20 μg/ml) of each of humanized antibody Nos. 5 (Production Example 6), 7 (Production Example 7), 15 (Production Example 8), 16 (Production Example 9), and 17 (Production Example 10) for 6 h. GLI1 Reporter activity (%) was measured through luminescence using a Reporter assay kit (Promega, WI, USA). The above procedure was repeated except that the SMO small-molecule inhibitor vismodegib or erismodegib was used as a positive control instead of the inventive SMO antibody.

3. Conclusion

Figure 20:
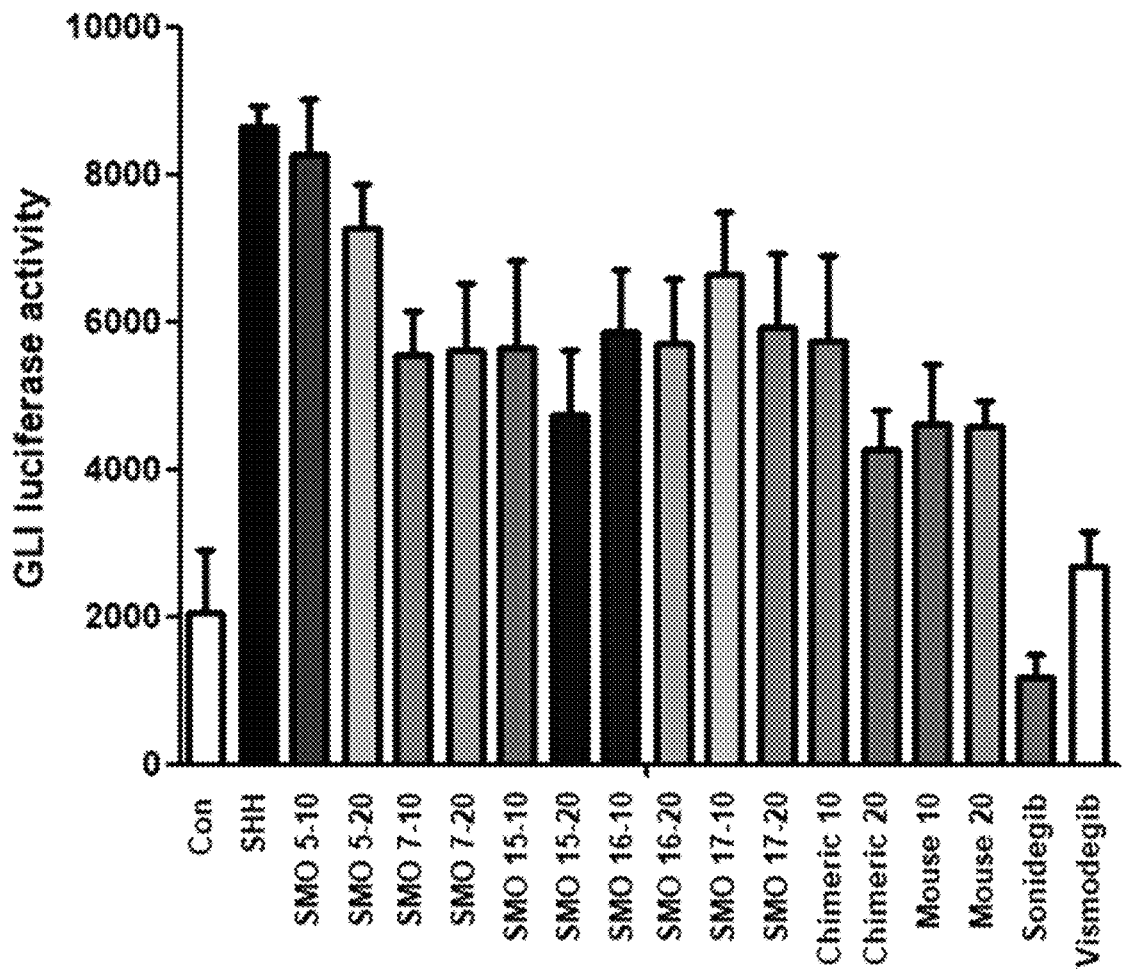
FIG. 20 shows the GLI reporter activities (%) of humanized SMO antibodies in NIH3T3-GLI cells.

FIG. 20 shows the GLI reporter activities (%) of the humanized SMO antibodies in NIH3T3-GLI cells. In FIG. 20, the numbers and concentrations of the humanized SMO antibodies are denoted. For example, "SMO 5-10" indicates treatment with 10 μg/ml of humanized SMO antibody No. 5.

Specifically, GLI is a downstream signaling component in the hedgehog signaling pathway and Gill Reporter activities were analyzed from NIH3T3-GLI cells treated with different substances to determine the transcriptional regulation ability of GLI. As a result, it was found that the use of inventive humanized SMO antibody Nos. 7, 15, 16, and 17 except for humanized SMO antibody No. 5 significantly inhibited the transcriptional activity of GLI, but not as much as the positive control treated with vismodegib or erismodegib. The GLI reporter activities were numerically similar to those of chimeric antibodies and mouse antibodies. The mouse antibodies were collected from hybridoma cells before conversion to the humanized antibody in Production Example 6.

The inventive humanized SMO antibodies (Nos. 5, 7, 15, 16, and 17) were confirmed to effectively inhibit the SHH-induced GLI transcriptional activity, revealing that treatment of the humanized SMO antibodies in a cell line where SMO expression is high can inhibit cell growth. In conclusion, the use of the inventive humanized SMO antibodies (Nos. 5, 7, 15, 16, and 17) is expected to be useful for personalized treatment.

<Example 15> Inhibition of GLI1 by the Humanized SMO Antibodies in Hedgehog Overexpressing Cell Lines 1. HCT116 Cell Line Culture and Antibody Treatment HCT116 cell line was purchased from the Korean Cell Line Bank. 24 h after cells were plated in a 100-well plate at a density of $5\times10^5$ cells/cm$^2$, they were treated with different concentrations (10 and 20 μg/ml) of each of humanized SMO antibody Nos. 5, 7, 15, 16, and 17 in serum free media.

2. Protein Isolation

Cells were disrupted by a combination of mechanical homogenization and sonication in a lysis buffer (7 M urea, 2 M thiourea, 4% CHAPS, 40 mM Tris, 100 mM DTT) supplemented with protease, followed by centrifugation at 15,000 rpm and 4° C. for 20 min. Proteins in the supernatant were quantified with NanoDrop by bicinchoninic acid (BCA) assay.

3. Western Blotting

30 μg of the proteins isolated from the collected tissues were subjected to electrophoresis, transferred to a PVDF membrane, labeled with anti-GLI1 antibody (cell signaling, MA, USA), anti-SMO antibody (Santa Cruz, CA, USA), and anti β-actin antibody as primary antibodies and an HRP-conjugated anti-rabbit antibody as a secondary antibody, and detected by chemiluminescence staining. The expression levels of SMO protein were measured by the enhanced chemiluminescence (ECL) method.

4. Conclusion

Figure 21:
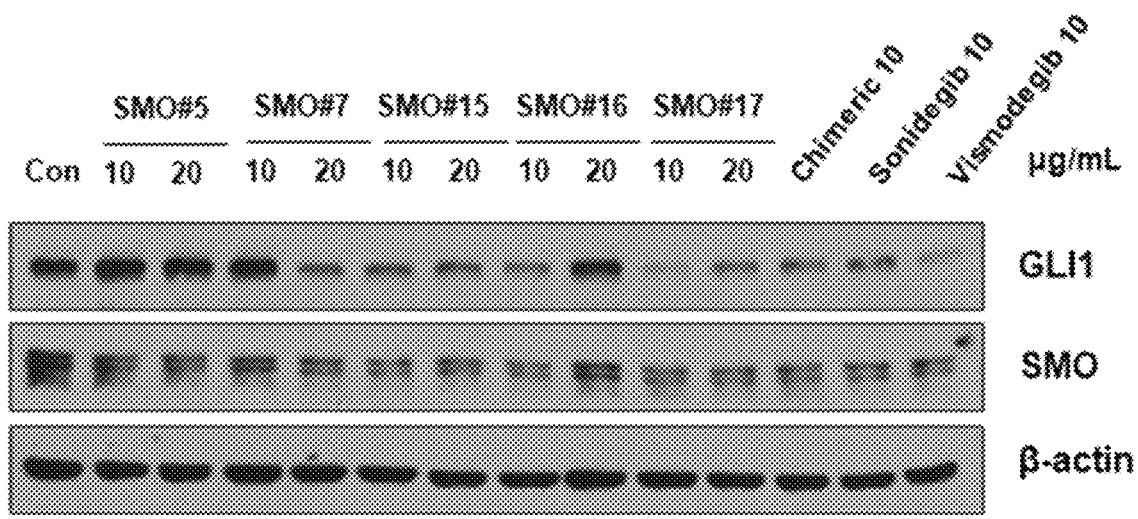
FIG. 21 shows images showing the results of Western blotting for HCT116 cell line.

FIG. 21 shows images showing the results of Western blotting for HCT116 cell line. As shown in FIG. 21, the treatment with humanized SMO antibody Nos. 7, 15, 16, and 17 was found to reduce the expression levels of GLI1 and SMO proteins.

<Example 16> Measurement of Cell Proliferations by the Humanized SMO Antibodies in Colorectal Cancer Cell Line 1. WST-1 method 24 h after colorectal cancer cells and normal cells were plated in 96-well plates, different concentrations (0, 10, and 20 μg/ml) of humanized SMO antibody Nos. 7, 15, 16, and 17 were added. Following 24 h, cells were incubated with WST-1 solution for 4 h and cell viability was assessed by measuring absorbance at 500 nm.

2. Conclusion

Figure 22:
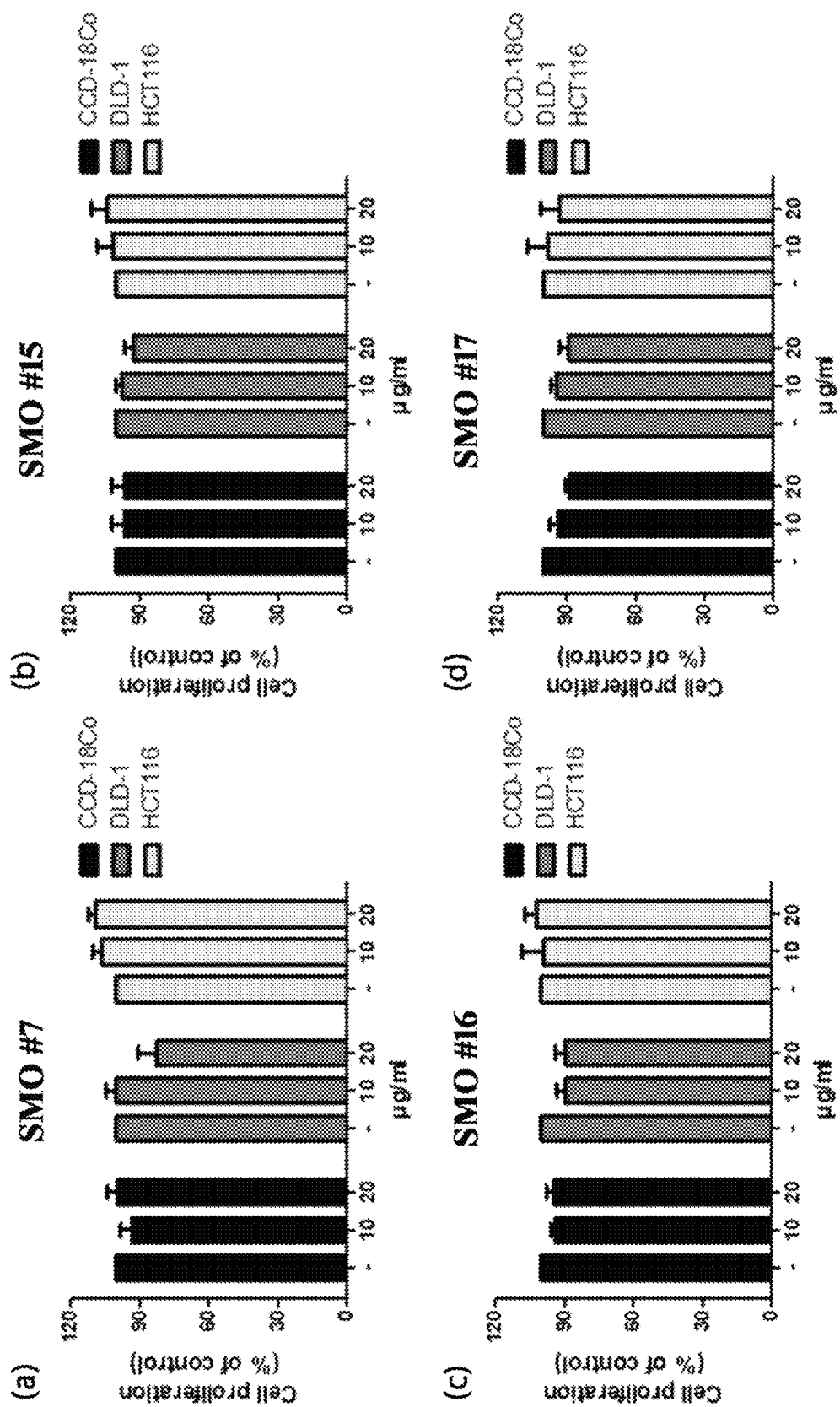
FIG. 22 shows the proliferations of normal and colorectal cancer cells treated with (a) humanized SMO antibody No. 7, (b) humanized SMO antibody No. 15, (c) humanized SMO antibody No. 16, and (d) humanized SMO antibody No. 7, which were measured by WST-1 assay.

FIG. 22 shows the proliferations of normal and colorectal cancer cells treated with (a) humanized SMO antibody No. 7, (b) humanized SMO antibody No. 15, (c) humanized SMO antibody No. 16, and (d) humanized SMO antibody No. 7, which were measured by WST-1 assay.

As shown in FIG. 22, no substantial changes in the growth of the normal colorectal cells (CCD-18Co) and the colorectal cancer cells (DLD-1, HCT116) were observed regardless of the presence or absence of the humanized SMO antibodies. In conclusion, the inventive humanized SMO antibodies do not affect the proliferation of colorectal cancer cells.

<Example 17> Measurement of Cell Motilities by the Humanized SMO Antibodies in HCT116 cell line 1. Transwell Migration Assay After HCT116 cell line was plated in a transwell, each of humanized SMO antibody Nos. 7, 15, 16, and 17 was added at a concentration of 10 μg/ml. Following 48 h, cell motility was measured using a Diff-Quik kit.

2. Conclusion

Figure 23A:
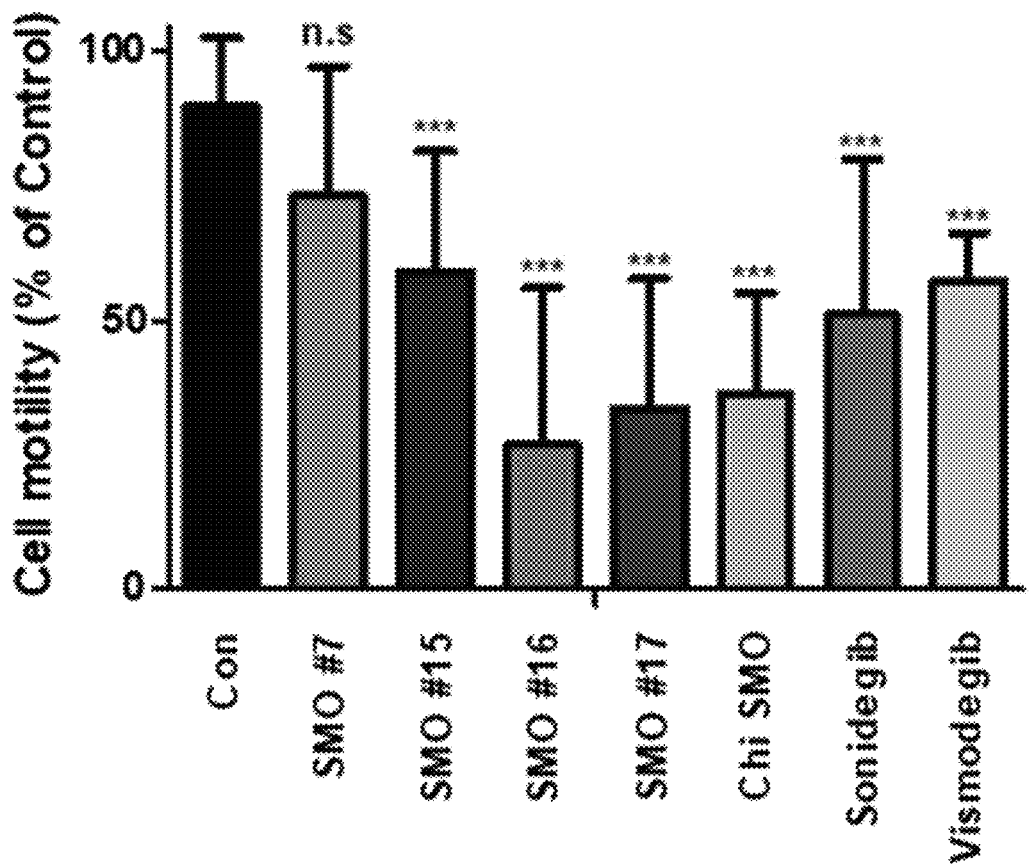
FIG. 23a shows the motilities of HCT116 cell line treated with humanized SMO antibody Nos. 7, 15, 16, and 17.
Figure 23B:
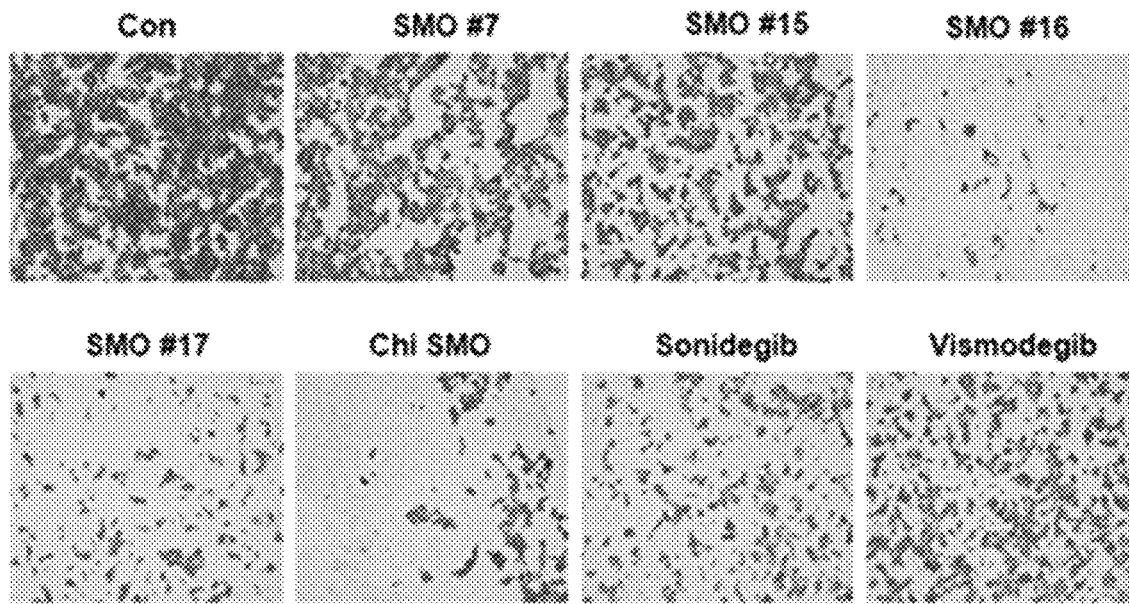
FIG. 23b shows optical microscopy images of HCT116 cell line treated with humanized SMO antibody Nos. 7, 15, 16, and 17, which were taken after the cells were immobilized and stained to measure their motilities.

FIG. 23a shows the motilities of the HCT116 cell line treated with humanized SMO antibody Nos. 7, 15, 16, and 17. FIG. 23b shows optical microscopy images of the HCT116 cell line treated with humanized SMO antibody Nos. 7, 15, 16, and 17, which were taken after the cells were immobilized and stained to measure their motilities. As shown in FIG. 23, the use of inventive antibody Nos. 16 and 17 significantly inhibited cell motility compared to the treatment with vismodegib or erismodegib (positive control). These results revealed that humanized SMO antibody Nos. 7, 15, 16, and 17 inhibited the expression of GLI1 and SMO proteins in cells, resulting in a reduction in cell motility. In conclusion, the inventive humanized SMO antibodies can effectively inhibit cancer metastasis.

Particularly, humanized SMO antibody Nos. 16 and 17 showed the highest activities to reduce cell mobility by inhibited GLI1, demonstrating that their inhibitory activities against cancer metastasis were highest.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

The invention claimed is:

1. An antibody or a fragment thereof recognizing a SMO epitope having the sequence set forth in any one of SEQ ID NOS: 2 to 15 as an antigen and binding specifically to the SMO epitope wherein the antibody comprises HCDR1 having the sequence set forth in SEQ ID NO: 16, HCDR2 having the sequence set forth in SEQ ID NO: 17, HCDR3 having the sequence set forth in SEQ ID NO: 18, LCDR1 having the sequence set forth in SEQ ID NO: 19, LCDR2 having the sequence set forth in SEQ ID NO: 20, and LCDR3 having the sequence set forth in SEQ ID NO: 21.

2. An antibody or a fragment thereof recognizing a SMO epitope having the sequence set form in any one of SEQ ID NOS: 2 to 15 as an antigen and binding specifically to the SMO epitope, wherein the antibody comprises (1) a heavy chain variable region (VH) comprising the sequence set forth in SEQ ID NO: 22 and a light chain variable region (VL) comprising the sequence set forth in SEQ ID NO: 27; (2) a heavy chain variable region (VH) comprising the sequence set forth in SEQ ID NO: 23 and a light chain variable region (VL) comprising the sequence set forth in SEQ ID NO: 28; (3) a heavy chain variable region (VH) comprising the sequence set forth in SEQ ID NO: 24 and a light chain variable region (VL) comprising the sequence set forth in SEQ ID NO: 29; (4) a heavy chain variable region (VH) comprising the sequence set forth in SEQ ID NO: 25 and a light chain variable region (VL) comprising the sequence set forth in SEQ ID NO: 29; or (5) a heavy chain variable region (VH) comprising the sequence set forth in SEQ ID NO: 26 and a light chain variable region (VL) comprising the sequence set forth in SEQ ID NO: 29.

3. A nucleic acid molecule encoding the antibody or fragment thereof according to claim 1.

4. A nucleic acid molecule encoding the antibody or fragment thereof according to claim 2.

5. A vector comprising the nucleic acid molecule according to claim 3.

6. A vector comprising the nucleic acid molecule according to claim 4.

7. A host cell comprising the vector according to claim 5.

8. A host cell comprising the vector according to claim 6.

9. A pharmaceutical composition for treating cancer, comprising, as an active ingredient, the antibody or fragment thereof according to claim 1.

10. A pharmaceutical composition for treating cancer, comprising, as an active ingredient, the antibody or fragment thereof according to claim 2.

11. A pharmaceutical composition for inhibiting cancer metastasis, comprising, as an active ingredient, the antibody or fragment thereof according to claim 1.

12. A pharmaceutical composition for inhibiting cancer metastasis, comprising, as an active ingredient, the antibody or fragment thereof according to claim 2.

13. A method for treating cancer, comprising administering the composition according to claim 11.

14. A method for treating cancer, comprising administering the composition according to claim 12.

15. A method for treating metastatic cancer, comprising administering the composition according to claim 11.

16. A method for treating cancer, comprising administering the composition according to claim 12.

17. A kit for quantifying SMO protein, comprising the antibody or fragment thereof according to claim 1.

18. A kit for quantifying SMO protein, comprising the antibody or fragment thereof according to claim 2.

* * * * *

SEQUENCE LISTING

```
<160> NUMBER OF SEQ ID NOS: 29

<210> SEQ ID NO 1
<211> LENGTH: 787
<212> TYPE: PRT
<213> ORGANISM: Unknown
<220> FEATURE:
<223> OTHER INFORMATION: Vertebrate Smoothened polypeptide comprising
      SEQ ID NO:4 (Human)

<400> SEQUENCE: 1

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
    130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
    210                 215                 220

Ala Glu His Gln Asp Met His Ser Tyr Ile Ala Ala Phe Gly Ala Val
225                 230                 235                 240
```

```
Thr Gly Leu Cys Thr Leu Phe Thr Leu Ala Thr Phe Val Ala Asp Trp
            245             250             255

Arg Asn Ser Asn Arg Tyr Pro Ala Val Ile Leu Phe Tyr Val Asn Ala
            260             265             270

Cys Phe Phe Val Gly Ser Ile Gly Trp Leu Ala Gln Phe Met Asp Gly
            275             280             285

Ala Arg Arg Glu Ile Val Cys Arg Ala Asp Gly Thr Met Arg Leu Gly
            290             295             300

Glu Pro Thr Ser Asn Glu Thr Leu Ser Cys Val Ile Ile Phe Val Ile
305             310             315             320

Val Tyr Tyr Ala Leu Met Ala Gly Val Val Trp Phe Val Val Leu Thr
            325             330             335

Tyr Ala Trp His Thr Ser Phe Lys Ala Leu Gly Thr Thr Tyr Gln Pro
            340             345             350

Leu Ser Gly Lys Thr Ser Tyr Phe His Leu Leu Thr Trp Ser Leu Pro
            355             360             365

Phe Val Leu Thr Val Ala Ile Leu Ala Val Ala Gln Val Asp Gly Asp
            370             375             380

Ser Val Ser Gly Ile Cys Phe Val Gly Tyr Lys Asn Tyr Arg Tyr Arg
385             390             395             400

Ala Gly Phe Val Leu Ala Pro Ile Gly Leu Val Leu Ile Val Gly Gly
            405             410             415

Tyr Phe Leu Ile Arg Gly Val Met Thr Leu Phe Ser Ile Lys Ser Asn
            420             425             430

His Pro Gly Leu Leu Ser Glu Lys Ala Ala Ser Lys Ile Asn Glu Thr
            435             440             445

Met Leu Arg Leu Gly Ile Phe Gly Phe Leu Ala Phe Gly Phe Val Leu
            450             455             460

Ile Thr Phe Ser Cys His Phe Tyr Asp Phe Phe Asn Gln Ala Glu Trp
465             470             475             480

Glu Arg Ser Phe Arg Asp Tyr Val Leu Cys Gln Ala Asn Val Thr Ile
            485             490             495

Gly Leu Pro Thr Lys Gln Pro Ile Pro Asp Cys Glu Ile Lys Asn Arg
            500             505             510

Pro Ser Leu Leu Val Glu Lys Ile Asn Leu Phe Ala Met Phe Gly Thr
            515             520             525

Gly Ile Ala Met Ser Thr Trp Val Trp Thr Lys Ala Thr Leu Leu Ile
            530             535             540

Trp Arg Arg Thr Trp Cys Arg Leu Thr Gly Gln Ser Asp Asp Glu Pro
545             550             555             560

Lys Arg Ile Lys Lys Ser Lys Met Ile Ala Lys Ala Phe Ser Lys Arg
            565             570             575

His Glu Leu Leu Gln Asn Pro Gly Gln Glu Leu Ser Phe Ser Met His
            580             585             590

Thr Val Ser His Asp Gly Pro Val Ala Gly Leu Ala Phe Asp Leu Asn
            595             600             605

Glu Pro Ser Ala Asp Val Ser Ser Ala Trp Ala Gln His Val Thr Lys
            610             615             620

Met Val Ala Arg Arg Gly Ala Ile Leu Pro Gln Asp Ile Ser Val Thr
625             630             635             640

Pro Val Ala Thr Pro Val Pro Pro Glu Glu Gln Ala Asn Leu Trp Leu
            645             650             655
```

```
Val Glu Ala Glu Ile Ser Pro Glu Leu Gln Lys Arg Leu Gly Arg Lys
                660                 665                 670

Lys Lys Arg Arg Lys Arg Lys Lys Glu Val Cys Pro Leu Ala Pro Pro
            675                 680                 685

Pro Glu Leu His Pro Ala Pro Ala Pro Ser Thr Ile Pro Arg Leu
        690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Pro Gln Asp Pro Phe Leu Pro Ser Ala
                740                 745                 750

Pro Ala Pro Val Ala Trp Ala His Gly Arg Arg Gln Gly Leu Gly Pro
            755                 760                 765

Ile His Ser Arg Thr Asn Leu Met Asp Thr Glu Leu Met Asp Ala Asp
        770                 775                 780

Ser Asp Phe
785

<210> SEQ ID NO 2
<211> LENGTH: 10
<212> TYPE: PRT
<213> ORGANISM: Artificial Sequence
<220> FEATURE:
<223> OTHER INFORMATION: SMO epitope

<400> SEQUENCE: 2

Leu Val Leu Trp Ser Gly Leu Arg Asn Ala
1               5                   10

<210> SEQ ID NO 3
<211> LENGTH: 9
<212> TYPE: PRT
<213> ORGANISM: Artificial Sequence
<220> FEATURE:
<223> OTHER INFORMATION: SMO epitope

<400> SEQUENCE: 3

Leu Leu Cys Ala Val Tyr Met Pro Lys
1               5

<210> SEQ ID NO 4
<211> LENGTH: 8
<212> TYPE: PRT
<213> ORGANISM: Artificial Sequence
<220> FEATURE:
<223> OTHER INFORMATION: SMO epitope

<400> SEQUENCE: 4

Arg Glu Arg Gly Trp Pro Asp Phe
1               5

<210> SEQ ID NO 5
<211> LENGTH: 9
<212> TYPE: PRT
<213> ORGANISM: Artificial Sequence
<220> FEATURE:
<223> OTHER INFORMATION: SMO epitope

<400> SEQUENCE: 5

Gln Cys Gln Asn Pro Leu Phe Thr Glu
1               5
```

<210> SEQ ID NO 6
<211> LENGTH: 9
<212> TYPE: PRT
<213> ORGANISM: Artificial Sequence
<220> FEATURE:
<223> OTHER INFORMATION: SMO epitope

<400> SEQUENCE: 6

Gly Thr Met Arg Leu Gly Glu Pro Thr
1               5

<210> SEQ ID NO 7
<211> LENGTH: 9
<212> TYPE: PRT
<213> ORGANISM: Artificial Sequence
<220> FEATURE:
<223> OTHER INFORMATION: SMO epitope

<400> SEQUENCE: 7

Phe Val Gly Tyr Lys Asn Tyr Arg Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: SMO epitope

<400> SEQUENCE: 8

Gln Ala Glu Trp Glu Arg Ser Phe Arg
1               5

<210> SEQ ID NO 9
<211> LENGTH: 16
<212> TYPE: PRT
<213> ORGANISM: Artificial Sequence
<220> FEATURE:
<223> OTHER INFORMATION: SMO epitope

<400> SEQUENCE: 9

Glu Glu Ala His Gly Lys Leu Val Leu Trp Ser Gly Leu Arg Asn Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: SMO epitope

<400> SEQUENCE: 10

Gly Ile Gln Cys Gln Asn Pro Leu Phe Thr Glu Ala Glu His Gln
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: SMO epitope

<400> SEQUENCE: 11

Pro Leu Leu Cys Ala Val Tyr Met Pro Lys Cys Glu Asn Asp Arg
1               5                   10                  15

```
<210> SEQ ID NO 12
<211> LENGTH: 14
<212> TYPE: PRT
<213> ORGANISM: Artificial Sequence
<220> FEATURE:
<223> OTHER INFORMATION: SMO epitope

<400> SEQUENCE: 12

Ala Ile Val Glu Arg Glu Arg Gly Trp Pro Asp Phe Leu Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: SMO epitope

<400> SEQUENCE: 13

Phe Asn Gln Ala Glu Trp Glu Arg Ser Phe Arg Asp Tyr Val
1               5                   10

<210> SEQ ID NO 14
<211> LENGTH: 15
<212> TYPE: PRT
<213> ORGANISM: Artificial Sequence
<220> FEATURE:
<223> OTHER INFORMATION: SMO epitope

<400> SEQUENCE: 14

Ile Cys Phe Val Gly Tyr Lys Asn Tyr Arg Tyr Arg Ala Gly Phe
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: SMO epitope

<400> SEQUENCE: 15

Ala Asp Gly Thr Met Arg Leu Gly Glu Pro Thr Ser Asn Glu
1               5                   10

<210> SEQ ID NO 16
<211> LENGTH: 5
<212> TYPE: PRT
<213> ORGANISM: Artificial Sequence
<220> FEATURE:
<223> OTHER INFORMATION: HCDR1

<400> SEQUENCE: 16

Glu Tyr Thr Met His
1               5

<210> SEQ ID NO 17
<211> LENGTH: 17
<212> TYPE: PRT
<213> ORGANISM: Artificial Sequence
<220> FEATURE:
<223> OTHER INFORMATION: HCDR2

<400> SEQUENCE: 17

Gly Ile Asn Pro Asn Thr Gly Asp Thr Arg Tyr Asn Gln Lys Phe Lys
1               5                   10                  15

Gly
```

<210> SEQ ID NO 18
<211> LENGTH: 9
<212> TYPE: PRT
<213> ORGANISM: Artificial Sequence
<220> FEATURE:
<223> OTHER INFORMATION: HCDR3

<400> SEQUENCE: 18

Asp Tyr Tyr Gly Ser Pro Phe Val Tyr
1               5

<210> SEQ ID NO 19
<211> LENGTH: 16
<212> TYPE: PRT
<213> ORGANISM: Artificial Sequence
<220> FEATURE:
<223> OTHER INFORMATION: LCDR1

<400> SEQUENCE: 19

Arg Ser Ser Gln Ser Ile Val His Ser Ser Gly Tyr Thr Phe Leu Asp
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: LCDR2

<400> SEQUENCE: 20

Lys Val Ser Asn Arg Phe Ser
1               5

<210> SEQ ID NO 21
<211> LENGTH: 9
<212> TYPE: PRT
<213> ORGANISM: Artificial Sequence
<220> FEATURE:
<223> OTHER INFORMATION: LCDR3

<400> SEQUENCE: 21

Phe Gln Gly Ser His Val Pro Leu Thr
1               5

<210> SEQ ID NO 22
<211> LENGTH: 118
<212> TYPE: PRT
<213> ORGANISM: Artificial Sequence
<220> FEATURE:
<223> OTHER INFORMATION: huSM01-21-05 VH

<400> SEQUENCE: 22

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Glu Tyr
            20                  25                  30

Thr Met His Trp Val Gln Gln Ala Pro Gly Lys Gly Leu Glu Trp Met
        35                  40                  45

Gly Gly Ile Asn Pro Asn Thr Gly Asp Thr Arg Tyr Asn Gln Lys Phe
    50                  55                  60

Lys Gly Arg Val Thr Ile Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

```
Ala Arg Asp Tyr Tyr Gly Ser Pro Phe Val Tyr Trp Gly Gln Gly Thr
            100                 105                 110

Leu Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: huSM01-21-07 VH

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Arg Leu Glu Trp Met
            35                  40                  45

Gly Gly Ile Asn Pro Asn Thr Gly Asp Thr Arg Tyr Asn Gln Lys Phe
        50                  55                  60

Lys Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Pro Phe Val Tyr Trp Gly Gln Gly Thr
            100                 105                 110

Leu Val Thr Val Ser Ser
        115

<210> SEQ ID NO 24
<211> LENGTH: 118
<212> TYPE: PRT
<213> ORGANISM: Artificial Sequence
<220> FEATURE:
<223> OTHER INFORMATION: huSM01-21-15 VH

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Gln Arg Leu Glu Trp Met
            35                  40                  45

Gly Gly Ile Asn Pro Asn Thr Gly Asp Thr Arg Tyr Asn Gln Lys Phe
        50                  55                  60

Lys Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Pro Phe Val Tyr Trp Gly Gln Gly Thr
            100                 105                 110

Leu Val Thr Val Ser Ser
        115

<210> SEQ ID NO 25
<211> LENGTH: 118
<212> TYPE: PRT
```

<213> ORGANISM: Artificial Sequence
<220> FEATURE:
<223> OTHER INFORMATION: huSM01-21-16 VH

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Ile Asn Pro Asn Thr Gly Asp Thr Arg Tyr Asn Gln Lys Phe
    50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Pro Phe Val Tyr Trp Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: huSM01-21-17 VH

<400> SEQUENCE: 26

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Glu Tyr
            20                  25                  30

Thr Met His Trp Val Gln Gln Ala Pro Gly Lys Gly Leu Glu Trp Met
        35                  40                  45

Gly Gly Ile Asn Pro Asn Thr Gly Asp Thr Arg Tyr Asn Gln Lys Phe
    50                  55                  60

Lys Gly Arg Val Thr Ile Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Pro Phe Val Tyr Trp Gly Gln Gly Thr
            100                 105                 110

Leu Val Thr Val Ser Ser
        115

<210> SEQ ID NO 27
<211> LENGTH: 112
<212> TYPE: PRT
<213> ORGANISM: Artificial Sequence
<220> FEATURE:
<223> OTHER INFORMATION: huSM01-21-05 VL

<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Ser Gly Tyr Thr Phe Leu Asp Trp Phe Gln Gln Arg Pro Gly Gln Ser
            35                  40                  45

Pro Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: huSM01-21-07 VL

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Ser Gly Tyr Thr Phe Leu Asp Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: huSM01-21-15 VL

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
                20                  25                  30

Ser Gly Tyr Thr Phe Leu Asp Trp Tyr Gln Gln Lys Pro Gly Lys Ala
            35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser His Val Pro Leu Thr Phe Gly Gln Gly Thr Lys Val Glu Ile Lys
            100                 105                 110